United States Patent [19]

Rogers et al.

[11] Patent Number: 5,359,053
[45] Date of Patent: Oct. 25, 1994

[54] MODIFIED DEAZAPYRIMIDINES

[75] Inventors: Thomas E. Rogers, Manchester; Steven H. Gray, Ellisville; Balekudru Devadas, Chesterfield; Steven P. Adams, St. Charles, all of Mo.

[73] Assignee: G. D. Searle & Co., Chicago, Ill.

[21] Appl. No.: 879,648

[22] Filed: May 6, 1992

Related U.S. Application Data

[63] Continuation of Ser. No. 400,205, Aug. 29, 1989, Pat. No. 5,134,066.

[51] Int. Cl.$^5$ .............. C07H 15/12; C07H 17/00; C07H 19/06
[52] U.S. Cl. ............... 536/28.4; 536/28.53; 536/28.54; 536/28.55; 536/24.3; 536/24.31; 536/24.32; 536/26.1; 536/26.8
[58] Field of Search ............... 435/6, 91, 805; 436/501; 536/23, 24, 27–29, 122, 124, 126, 28.4, 28.53, 28.54, 26.8, 28.55, 24.3, 24.31, 24.32, 26.1; 546/290, 296, 302, 303, 345, 353; 935/78, 88, 86

[56] References Cited

U.S. PATENT DOCUMENTS

| | | | |
|---|---|---|---|
| 3,705,147 | 12/1972 | Robbins et al. | 260/211.5 |
| 3,748,320 | 7/1973 | Vorbruggen et al. | 536/28.54 |
| 3,856,777 | 12/1974 | Ishido et al. | 536/28.54 |
| 3,873,516 | 3/1975 | Kotick et al. | 536/28.54 |
| 4,211,773 | 7/1980 | Lopez et al. | 536/28.54 |
| 4,321,366 | 3/1982 | Bobek et al. | 536/28.1 |
| 4,334,059 | 6/1982 | Ogilivie | 536/28.1 |
| 4,556,643 | 12/1985 | Paau et al. | 436/501 |
| 4,563,417 | 1/1986 | Albarella et al. | 435/6 |
| 4,599,303 | 7/1986 | Yabusaka et al. | 435/6 |
| 4,605,735 | 8/1986 | Miyoshi et al. | 536/27 |
| 5,006,646 | 4/1991 | Itoh et al. | 536/23 |
| 5,015,733 | 5/1991 | Smith et al. | 536/23 |
| 5,093,232 | 3/1992 | Urdea et al. | 536/6 |

FOREIGN PATENT DOCUMENTS

| | | | |
|---|---|---|---|
| 9093095 | 5/1984 | Japan | 536/28.1 |
| 937459 | 6/1982 | U.S.S.R. | 536/27.81 |

OTHER PUBLICATIONS

M. C. Wang et al., *Biochemical Pharmacology* 21:1063 (1972).

H. Schetters et al., *Biochimia Et Biophysica ACTA* 272:549 (1972).

Amarnath et al. *Nucleosides & Nucleotides*, 1(2). 163–171 (1982).

*Primary Examiner*—Douglas W. Robinson
*Assistant Examiner*—L. Blaine Lankford
*Attorney, Agent, or Firm*—Dennis A. Bennett

[57] ABSTRACT

The probes of the invention are able to withstand higher temperatures, thereby allowing unmatched probes and mismatched probes to be washed off at higher hybridization stringency, thereby eliminating background readings and improving ease and accuracy of probe use.

10 Claims, No Drawings

MODIFIED DEAZAPYRIMIDINES

This is a continuation application of co-pending application Ser. No. 400,205, filed Aug. 29, 1989 now U.S. Pat. No. 5,134,066.

BACKGROUND OF THE INVENTION

This invention is directed to novel nucleic acid probes that can be used with stringent hybridization conditions thereby decreasing background readings and improving the ease and accuracy of probe use.

In recombinant DNA technology and related fields such as diagnostics it is necessary to possess means for detecting specific nucleic acid sequences. The basic building blocks from which nucleic acids are constructed are nucleotides. The major nucleotides found in living cells are adenosine, guanosine, cytidine, thymidine and uridine. Nucleic acids contain the information for the transfer of genetic information from one generation to the next, as well as for the expression of this information through protein synthesis. Therefore, genetic materials can be evaluated and manipulated on the basis of nucleotide sequences. Based on this understanding of genetic makeup, probes can be designed to perform a variety of functions in the field of recombinant DNA technology and related areas.

Probes are oligomeric or polymeric nucleic acid molecules with complementary sequences to a nucleic acid sequence of interest. Through the use of probes, the ability to identify, localize, and detect nucleic acid sequences can be readily accomplished. Probes are not only useful in laboratory techniques and diagnostics, but are also useful in the field of therapeutics.

Typically, probes are used in determining the presence of a specific nucleic acid sequence. This involves digesting DNA or RNA with restriction endonucleases to produce smaller fragments. The fragments are separated by molecular weight and transferred and bound to a filter. The filter is then incubated with labelled probes consisting of single strands of DNA or RNA with nucleotide sequences complementary to a specific region in the DNA or RNA that is being detected. If the labelled probe binds to one of the nucleic acid bands on the filter, the sequence of interest resides in that band. Thus, probes may be used to determine the presence of specific genes, pathogens, human and non-human DNA or RNA, natural or foreign DNA or RNA and a variety of other detectable compositions.

Whether a hybrid nucleic acid molecule forms accurately between a probe and target sequence depends on two important factors. The probe should bind only to the desired target sequence, and the hybrid nucleic acid molecule thus formed should be correctly and sensitively identified. Therefore, it is of great advantage to have a probe that is both capable of recognizing and hybridizing to only its complement and is also capable of being accurately and sensitively identified.

The use of probes in determining the presence of specific genomic regions has been possible for some time, see Southern, *J. Mol. Biol.*, 98:503, 1975. Albarella et al., U.S. Pat. No. 4,563,417, describe hybridization which occurs between sample nucleic acid and the probe in nucleic acid hybridization assays detected by an antibody that binds to intercalation complexes formed in association with hybridized probe. The use of probes containing psoralen derivatives that form covalent bonds with the target DNA when photochemically activated has been described in Yabusaki et al., U.S. Pat. No. 4,599,303. Specific DNA probes in diagnostic microbiology have been disclosed in Falkow et al., U.S. Pat. No. 4,358,535. There are a variety of probes available for detection of a variety of nucleic acid sequences. Despite the variety of probe strategies available, it would greatly improve probe use to have a probe capable of withstanding stringent hybridization conditions to eliminate background readings and to improve the ease, accuracy and sensitivity of probe use.

SUMMARY OF THE INVENTION

The invention relates to single-stranded nucleic acid probes which comprise a nucleoside residue of the formula:

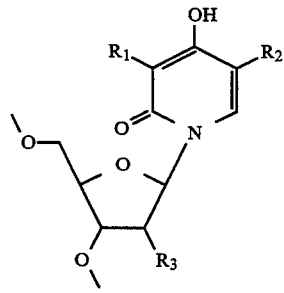

in which $R_1$ and $R_2$ independently are $C_1$–$C_5$ alkyl, $C_2$–$C_5$ alkenyl, halo or hydrogen, and $R_3$ is hydrogen, hydroxy, $C_6$–$C_{14}$ aryloxy or $C_1$–$C_5$ alkoxy.

In preferred probes of the invention only one $R_1$ or $R_2$ is substituted. Preferred $R_1$ and $R_2$ substituents are iodo or vinyl. In more preferred probes of the invention $R_1$, $R_2$ and $R_3$ are hydrogen.

The nucleoside residue is drawn to indicate bonding between the 3' and 5' positions of the ribose or deoxyribose. The nucleoside residue of the invention is situated in the probe to be complementary to a guanosine residue (where a cytidine would normally reside) of a target sequence. Typically, probes of the invention are molecules of about 15 to 50 nucleotides in which a nucleoside residue of the invention is at least five (5) nucleotides from both ends of the molecule. Preferred probes of the invention are molecules of 15 to 25 nucleotides. Theoretically, there is no maximum length for a probe of the invention, however, in order to obtain reasonable hybridization times, probes of 100 nucleotides or less are recommended.

As used herein, "hybridization" refers to the process in which a strand of nucleotide sequences binds with complementary sequences through base pairing. "Hybrid molecule" refers to the complex resulting from hybridization. Further, as used herein, "complementary sequences" refers to sequences of nucleotides that are capable of base pairing. Furthermore, "base pairing" refers to the interaction, through hydrogen bonding, that occurs between opposite purine and pyrimidine bases in nucleic acids. Nucleotides that form stable base pairs are adenosine and thymidine (uridine in RNA), and guanosine and cytidine. Base pairing may occur between two complementary strands of DNA (DNA/DNA), between two RNA strands (RNA/RNA), or between one strand of each (DNA/RNA). "Target sequence" or "target nucleic acid sequence", as used herein, is defined as the region to which a probe is complementary. DNA, and RNA, as used herein, refer to nucleic acids with a naturally occurring sugar-phosphate backbone and also modified backbones including phosphorothioates, dithionates, alkyl phosphonates, phosphonates, phosphoramidates, hydrogen phosphonates and α-nucleotides. Compounds of the invention herein are named, then followed by a number in parenthesis corresponding to its structure as set forth in Tables I and II.

A probe may contain more than one nucleoside residue of the invention or combinations thereof. Preferably, there are intervening nucleotides separating each nucleoside residue of the invention in a probe. For example, a 30 mer probe could have a nucleoside residue of the invention at the 8th and 21st nucleotide. In addition, the invention may be used in either deoxyribonucleic acid probes or ribonucleic acid probes.

To make a probe of the invention, a probe is constructed to be complementary to a target sequence of interest. At a position in the probe that is complementary to a guanosine residue of the target sequence (therefore, at a position in the probe where a cytidine would normally be found), a nucleoside residue of the invention is substituted therefore. The resulting probe contains a nucleoside residue of the invention complementary to a guanidine in the target sequence. The nucleoside residue of the invention is generally placed at least five (5) nucleotides from both ends of the probe. While not wishing to be bound or limited by theory, it is believed that when such a substitution is made, the nucleoside residue of the invention is capable of forming a covalent bond with the target sequence to which it hybridizes. The hybrid molecules made by using probes of this invention and immobilized on filters can be washed at high temperatures where probes not containing a nucleoside residue of the invention wash off of the target sequence at the same temperature. Consequently, probes of the invention offer better specificity and the separation and removal of unhybridized material is greatly enhanced. The efficient removal of incorrectly hybridized probes eliminates background readings and enhances the detectability of correctly hybridized target sequences. Thus, a probe of the invention can be used with both improved ease and accuracy over probes without a nucleoside of the invention. It is anticipated that various substitutions to enhance bonding and stability between the nucleosides of the invention and the complementary strand may be made.

The invention further relates to compounds which are useful as intermediates in the preparation of probes of the invention. These compounds have the formula:

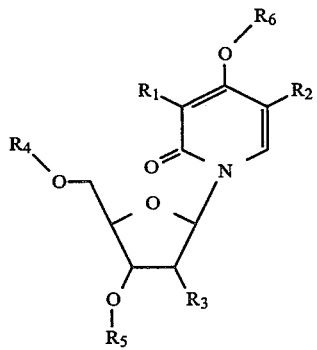

in which $R_1$ and $R_2$ independently are $C_1-C_5$ alkyl, $C_2-C_5$ alkenyl, halo or hydrogen, $R_3$ is hydrogen, halo, $C_1-C_5$ alkoxy or tri($C_1-C_5$ alkyl )substituted silyloxy, $R_4$ is triphenylmethyl, or mono-, di- or tri($C_1-C_5$ alkoxy)substituted triphenylmethyl, $R_5$ is hydrogen phosphonate or

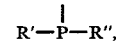

in which $R'$ is β-cyanoethoxy, $C_1-C_5$ alkoxy or $C_1-C_5$ alkyl and $R''$ is morpholino, or mono- or di($C_1-C_5$ alkyl)substituted amino, $R_6$ is tri($C_1-C_5$ alkyl or $C_1-C_5$ alkoxy) substituted silyl, benzoyl, methylcarbonyl, carbamoyl, or carbamoyl substituted with $C_1-C_5$ alkyl, phenyl, acetyl or isobutyryl.

Examples of suitable alkyl radicals include methyl, ethyl, propyl, isopropyl, butyl, sec-butyl, isobutyl, t-butyl, pentyl, isopentyl, and 1-methyl-1butyl. Examples of suitable alkenyl radicals include vinyl, 1-propenyl, 2-propenyl, isopropenyl, 1-butenyl, 2-butenyl, isobutenyl, 2-methyl-2-butenyl, 1-pentenyl, 2-pentenyl, 3-pentenyl, 4-pentenyl, and isopentenyl.

Examples of suitable alkoxyl radicals include methoxy, ethoxy, propoxy, butoxy and pentoxy. Examples of suitable tri-substituted silyl radicals include triisopropylsilyl, trimethylsilyl, and t-butyldimethylsilyl. Examples of suitable mono-, di- and tri-alkoxy substituted triphenylmethyl includes p-methoxytriphenylmethyl, p-dimethoxytriphenylmethyl, and p-trimethoxytriphenylmethyl. Examples of suitable di-alkyl substituted amino groups include N,N-diisopropylamino, N,N-dimethylamino, and N,N-diethylamino. Examples of suitable $C_6-C_{14}$ aryloxy includes phenoxy, 2-methylphenoxy, 4-methylphenoxy, 2,4-dimethylphenoxy, and naphthoxy. Examples of suitable substituted carbamoyl radicals are diphenylcarbamoyl, diisopropylcarbamoyl and dimethylcarbamoyl.

Illustrative compounds of the invention are listed below in Table I.

TABLE 1

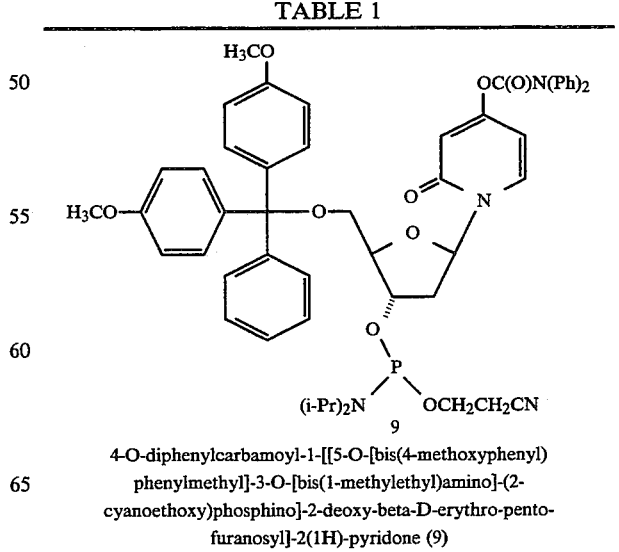

4-O-diphenylcarbamoyl-1-[[5-O-[bis(4-methoxyphenyl) phenylmethyl]-3-O-[bis(1-methylethyl)amino]-(2-cyanoethoxy)phosphino]-2-deoxy-beta-D-erythro-pentofuranosyl]-2(1H)-pyridone (9)

TABLE 1-continued

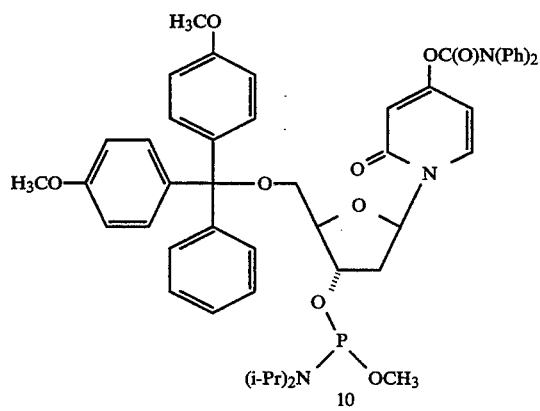

4-O-diphenylcarbamoyl-1-[[5-O-[bis(4-methoxyphenyl)
phenylmethyl]-3-O-[bis(1-methylethyl)amino]-methoxy-
phosphino]-2-deoxy-beta-D-erythro-pentofuranosyl]-
2(1H)-pyridone (10)

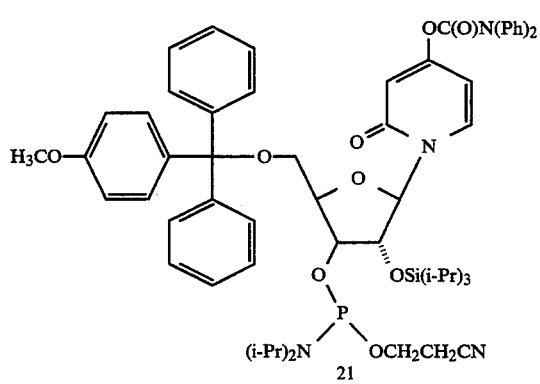

4-O-diphenylcarbamoyl-1-[[[5-O-[(4-methoxyphenyl)
diphenylmethyl]-3-O-[bis(1-methylethyl)amino]
(2-cyanoethyl)phosphino]-2-O-tris(1-methylethyl)silyl]-
beta-D-erythro-pentofuranosyl]-2(1H)-pyridone (21)

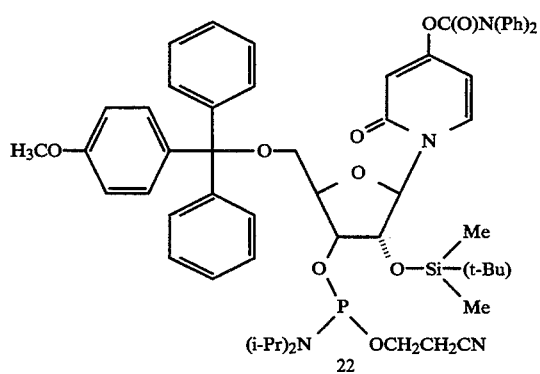

4-O-diphenylcarbamoyl-1-[[[5-O-[(4-methoxyphenyl)
diphenylmethyl]-3-O-[bis(1-methylethyl)amino](2-
cyanoethyl)phosphino]-2-O-(1,1-methylethyl)
dimethylsilyl]-beta-D-erythro-pentofuranosyl]-2(1H)-pyridone (22)

TABLE 1-continued

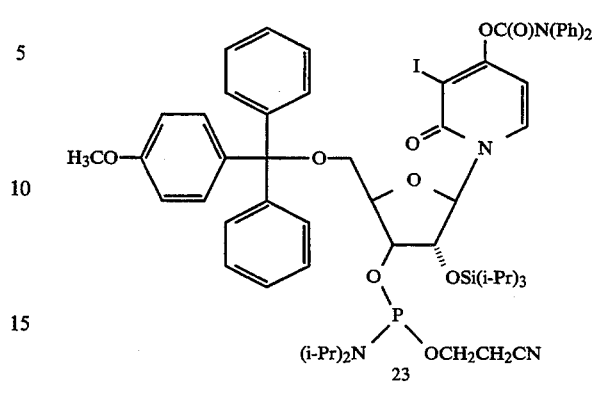

4-O-diphenylcarbamoyl-3-iodo-1-[[[5-O-[(4-methoxyphenyl)
diphenylmethyl]-3-O-[bis(1-methylethyl)amino](2-cyanoethyl)
phosphino]-2-O-tris(1-methylethyl)silyl]-beta-D-erythro-
pentofuranosyl]-2(1H)-pyridone (23)

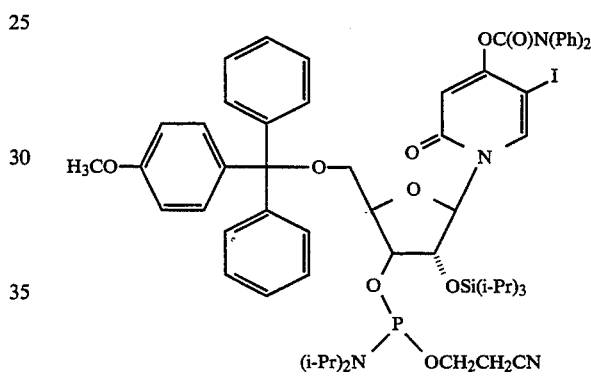

4-O-diphenylcarbamoyl-5-iodo-1-[[[5-O-[(4-methoxyphenyl)
diphenylmethyl]-3-O-[bis(1-methylethyl)amino](2-cyanoethyl)
phosphino]-2-O-tris(1-methylethyl)silyl]-beta-D-erythro-
pentofuranosyl]-2(1H)-pyridone (24)

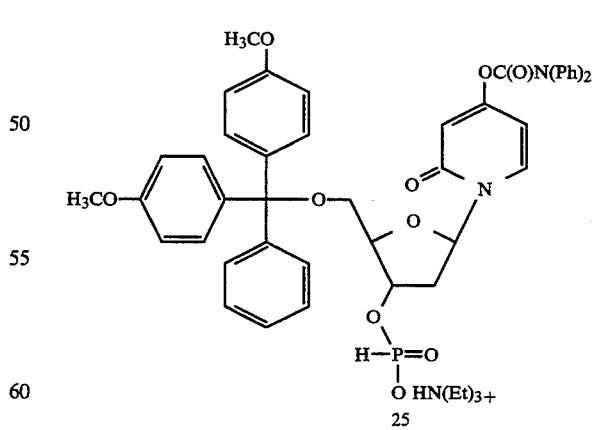

4-O-diphenylcarbamoyl-1-[[[5-O-[bis(4-methoxyphenyl)
phenylmethyl]-3-O-(hydroxyphosphinyl)-2-deoxy]-
beta-D-erythro-pentofuranosyl]-2(1H)-pyridone tri-
ethylammonium salt (25)

TABLE 1-continued

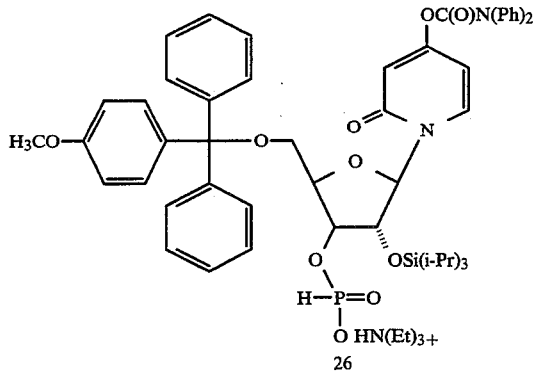

4-O-diphenylcarbamoyl-1-[[5-O-[(4-methoxyphenyl)
diphenylmethyl]-3-O-(hydroxyphosphinyl)-2-O-(tris-
(1-methylethyl)silyl]-beta-D-erythro-pentofuranosyl]-
2(1H)-pyridone triethylammonium salt (26)

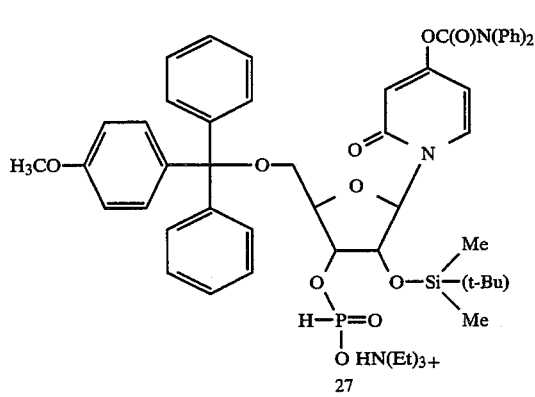

4-O-diphenylcarbamoyl-1-[[5-O-[(4-methoxyphenyl)
diphenylmethyl]-3-O-(hydroxyphosphinyl)-2-O-(1,1-
dimethylethyl)dimethylsilyl]-beta-D-erythro-pento-
furanosyl]-2(1H)-pyridone triethylammonium salt (27)

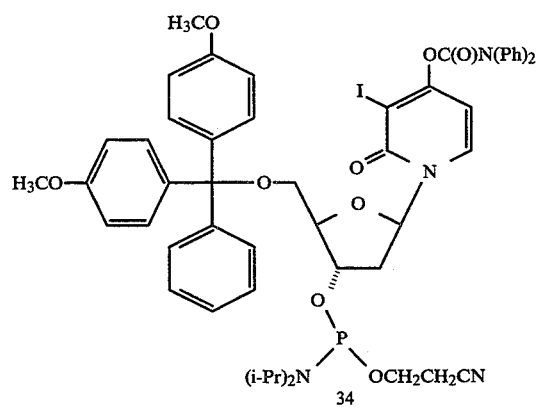

4-O-diphenylcarbamoyl-3-iodo-1-[5-O-[bis
(4-methoxyphenyl)phenylmethyl]-[3-O-[bis(1-
methylethyl)amino](2-cyanoethoxy)phosphino]-2-
deoxy-beta-D-erythro-pentofuranosyl]-2(1H)-pyridone (34)

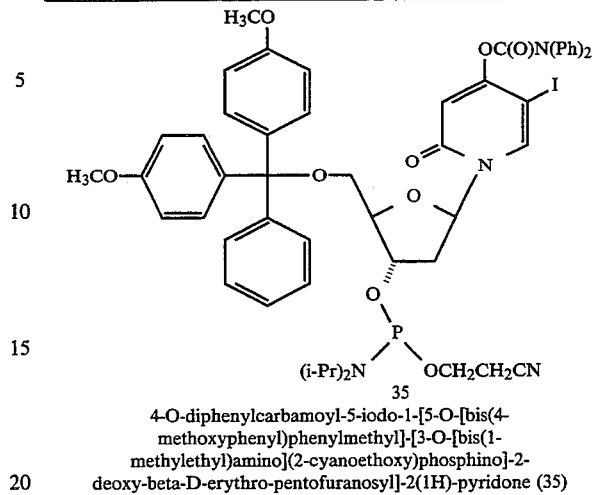

4-O-diphenylcarbamoyl-5-iodo-1-[5-O-[bis(4-
methoxyphenyl)phenylmethyl]-[3-O-[bis(1-
methylethyl)amino](2-cyanoethoxy)phosphino]-2-
deoxy-beta-D-erythro-pentofuranosyl]-2(1H)-pyridone (35)

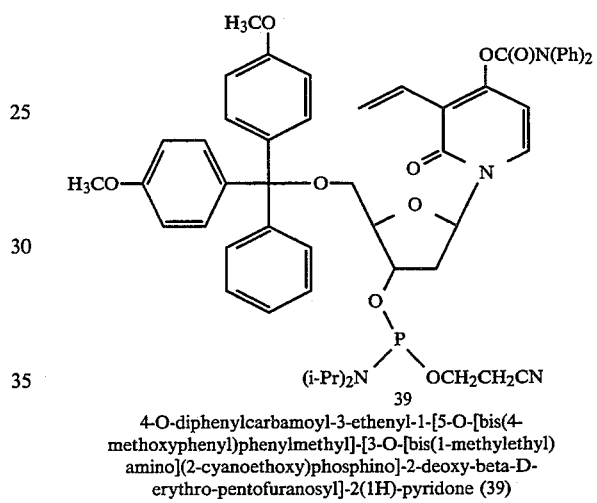

4-O-diphenylcarbamoyl-3-ethenyl-1-[5-O-[bis(4-
methoxyphenyl)phenylmethyl]-[3-O-[bis(1-methylethyl)
amino](2-cyanoethoxy)phosphino]-2-deoxy-beta-D-
erythro-pentofuranosyl]-2(1H)-pyridone (39)

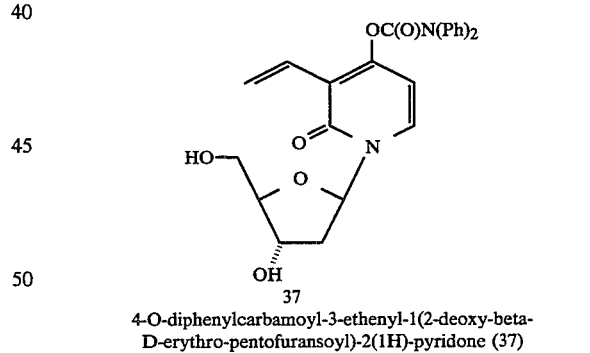

4-O-diphenylcarbamoyl-3-ethenyl-1(2-deoxy-beta-
D-erythro-pentofuransoyl)-2(1H)-pyridone (37)

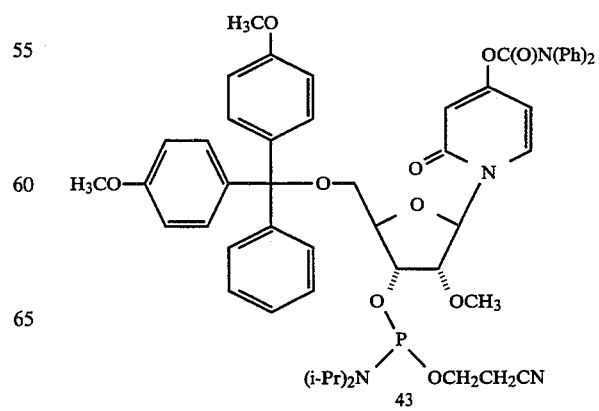

TABLE 1-continued

4-O-diphenylcarbamoyl-1-[5-O-[bis(4-methoxyphenyl)
phenylmethyl]-3-O-[bis(1-methylethyl)amino(2-
cyanoethoxy)phosphino]-2-O-methyl-beta-D-erythro-
pentofuranosyl]-2(1H)-pyridone (43)

Typically, the ratio of the extent of hybridization of perfect and mismatched duplexes is critically dependent upon the temperatures at which hybridization and washing are carried out. Such critical dependence on temperature leads to compromise between the higher temperatures required to achieve dissociation of mismatched duplexes and the lower temperatures needed to give the greatest degree of binding and, therefore, the highest sensitivity. However, when hybridization takes place between a probe of the invention and a complementary nucleic acid sequence, the resulting hybrid molecule exhibits enhanced stabilization resulting in higher melting temperatures, sometimes 25° C. higher, or more, than a corresponding hybrid molecule formed without a probe of the invention. Therefore, after hybridization, uncomplexed probe and mismatched complexes will be washed off at higher stringency conditions, thereby virtually eliminating all background readings and improving the ease and accuracy of probe use.

In order to incorporate a nucleoside residue of the invention into a probe, in place of one or more cytidine, the nucleoside is converted to a phosphoramidite derivative that is appropriately protected for DNA synthesis. See S. P. Adams et al., *J. Am. Chem. Soc.*, 105:661 (1983), L. J. McBride and M. H. Caruthers, *Tetrahedron Lett.*, 24:245 (1983), and N. D. Sinha et al., *Nucleic Acids Res.*, 12:4539 (1984). It is anticipated that all protecting groups will serve the same function of appropriately protecting the various groups of the nucleoside. Examples of appropriate protecting groups include triisopropylsilyloxy, t-butyl-dimethylsilyloxy, methoxyl, dimethoxytriphenylmethyl, triphenylmethyl (trityl), monomethoxytriphenylmethyl, trimethoxytriphenylmethyl, pixyl, N,N-diisopropylamine, morpholino, N,N-diethylamino, N,N-dimethylamine, methyl, β-cyanoethyl, hydrogen phosphonate, di-o-anisyl-1-napthylmethyl, and p-anisyl-1-napthylphenylbutyl.

An example of such a phosphoramidite derivative is the 2'-deoxy-3-deazauridine derivative, 4-O-diphenyl-carbamoyl-1- [[5-O-[bis(4-methoxyphenyl)phenylmethyl]-3-O-[bis(1-methyl ethyl) amino]-(2-cyanoethoxy)-phosphino]-2-deoxy-beta-D-erythro-pentofuranosyl]-2(1H )pyridone (9). The nucleic acids that may be used for purposes of practicing the invention include both the naturally occurring sugar-phosphate backbones as well as modified backbones as generally illustrated by Miller and T'so, *Ann. Reports Med. Chem.*, 23:295 (1988) and Moran et al., *Nuc. Acids Res.*, 14:5019 (1987). Likewise, the ribose forms of the nucleoside of the invention are also converted to the phosphoramidite form with appropriate protection of the 2' hydroxyl group before being placed into a nucleic acid probe. Methods for incorporating the phosphoramidite into a nucleic acid strand include the use of solid phase, solution phase triesters and H-phosphonate intermediates as generally illustrated by Froehler et al., *Nuc. Acids Res.*, 14:5399 (1986), Narang et al., *Methods Enz.*, 68:90 (1979) and Ogilvie, K. K. et al., *Proc. Natl. Acad. Sci. USA*, 85:5764 (1988).

After making a probe of the invention, the probe may be used to detect a target sequence. The particular hybridization technique for locating a target sequence is not essential to the invention. Typically, hybridization with a normal probe proceeds at about 5° C. to 10° C. below the melting temperature (Tm) of a normal phosphodiester probe. Usually, hybridization is carried out in a buffered solution between about pH 6 to 8. Optimal hybridization conditions may be determined empirically. Hybridization for a probe of the invention is carried out in a similar manner.

An important advantage of the probes of this invention is that the resulting hybrid molecules have significantly higher melting temperatures than corresponding hybrid molecules which contain no probes of the invention. This higher melting temperature permits higher wash temperatures than can be employed for probes without a nucleoside residue of the invention, for example, 50°-100° C., preferably between about 65°-85° C. Higher temperature washing gives cleaner and faster results because mismatched probes are unable to withstand the higher wash temperatures and are removed by the wash solution.

In addition to hybridizing probes as described above, a probe can be hybridized to target nucleic acid in solution. Moreover, the probe or target can be immobilized on a solid support and hybridized with target or probe, whichever one choses. Hybridization conditions may have varying degrees of stringency. Stringency is affected by temperature, probe length, ionic strength and other related factors. Nevertheless, by using a probe of the present invention, as long as hybridization is achieved, with any hybridization protocol employed, unmatched and mismatched probes may be removed under conditions that would normally also lead to the loss of the hybridized probe not containing a nucleoside residue of the invention. Probes will often hybridize to nucleic acid sequences that are similar to the target sequence but that are not of interest. Hybridization of this type is responsible for much of the background encountered when using normal DNA probes lacking a nucleoside residue of the invention. There are a variety of methods for removing non-hybridized probes from the hybridization process. Such methods include gel filtration, enzymatic digestion of all single-stranded nucleic acids, and washings consisting of buffer rinses at increased temperatures.

Probe detection methods include Northern blots, Southern blots and dot blots. Actual detection of hybridized probes is accomplished by measuring the label on the hybridized probes after removal of all non-hybridized and mismatched probes. The more common radioactive labels of choice include phosphorus 32 ($^{32}P$), tritium ($^{3}H$), carbon-14 ($^{14}C$), sulfur 35 ($^{35}S$), and fluorescent labels, chemiluminescent labels, and labels recognized by antibodies which are themselves labelled may also be used. The particular label used is a matter of choice. The manner in which a label is bound to the probe will vary depending upon the nature of the label chosen. In addition, a variety of methods are well known for introducing and measuring the various labels. Such methods include detection by radioscintillation counting, spectroscopy, such as fluorescence and luminescence, by immunological means and by chemical means.

A probe of the invention may be used in primer extension procedures or in screening genomic libraries. Target sequences can be on the order of several hundred to several thousand nucleotides. A probe of the invention is capable of hybridizing to target sequences of great length. As long as the probe and target sequence are capable of hybridizing to form a stable duplex, there is no target sequence too long to which a probe of the invention can be designed to hybridize. Likewise, probe length is only limited by the ability to hybridize and form a duplex to a target sequence. A suitable length of probe is about 15 to 50 bases in length with a preferred length being about 15 to 25 bases in length. Methods for identifying target sequences and for preparing probe regions are well known. The target sequences can be from any DNA or RNA sequence, either procaryote or eucaryote including bacteria, yeast, plants and animals, these include sequences of infectious microorganism, virus, or organism including parasites, human or non-human (animal) DNA or RNA sequences such as sequences characteristic of a genetic abnormality or other condition, and sequences derived from genetic engineering experiments such as total mRNA or random fragments of whole cell DNA. Nucleic acid sequences may be obtained from a variety of sources including blood, tissue and cell samples, as well as DNA from the same sources amplified by such means as the polymerase chain reaction (PCR). Toxin producing microorganisms like Escherichia, Vibrio, Yersivea, Klebsiella and Salmonella may be identified also. Specific species include *Haemophilis ducrei, Vibris cholerae,* and *E. coli.* Other agents of clinical importance include *Chlamydia trachomatous, genital Herpes virus, norwalk agent, Rotavirus, Campylabacter jejuni, Neisseria gonorrhea, Herpes simplex virus, Brucella abortus, Haemophilis influenza, Mycobacterium, tuberculosis, Pseudomonas pseudomallei, Salmonella typhi, Salmonella typhimurium, Neisseria meningitidis,* Epstein-Barr virus, and human papilloma virus. In addition, the target sequence can be complementary to a nucleic acid sequence which is characteristic of a class of human or non-human pathogens, like all enteric bacilli or all chlamydia. The target sequence can be complementary to a nucleic acid sequence which is characteristic of a host cell or vector used in the manufacture of recombinant DNA products, such as to detect the presence of such DNA or RNA contaminants in the product. Such detection may be useful in both diagnostics and therapeutics.

In some instances of probe use, it is desired to differentiate between a single nucleotide mismatch of the target sequence and probe. A probe of the invention can be designed so that hybridization with a target sequence resulting in a single nucleotide mismatch will be removed, leaving only the desired target sequence and probe hybridized molecule. Since a substantial number of human genetic diseases are caused by single point mutations, the probes of the present invention can be used to determine genotypes and aid in the diagnosis of genetic diseases, even prenatally.

Sickle cell anemia and α1-antitrypsin deficiency are examples of diseases arising from single point mutations. The following probe use, based on the sequence disclosure in Conner et al., *Proc. Natl. Acad. Sci.,* 80: 278, 1983, illustrates how a probe containing a nucleoside of the invention, 4-hydroxy- 1- (2-deoxy-beta-D-erythro-pentofuranosyl)-2(1H)-pyridone (2), commonly named 2'-deoxy-3deazauridine or DdU (when $R_1$, $R_2$ and $R_3$ are hydrogen in the nucleoside residue formula) can be used to detect the presence of a normal β-globin gene and the defective β-globin gene responsible for sickle cell anemia. Adenosine, thymidine, cytidine and guanosine are designated A, T, C and G respectively. A segment of the normal gene for β-globin has the following sequence:

```
            *
5' CT CCT GAG GAG AAG TCT GC 3'
3' GA GGA CTC CTC TTC AGA CG 5'
``` therefore examples of probes for the normal β-globin gene may have the following sequences:

```
3' GA GGA CTY CTC TTC AGA CG 5'
   GA GGA YTC CTC TTC AGA CG
   GA GGA CTC YTC TTC AGA CG
   GA GGA CTC CTY TTC AGA CG
Y = 2'-deoxy-3-deazauridine
```

A defective β-globin gene responsible for sickle cell disease has a single base mutation in the starred position of the normal gene sequence where the A (starred) is changed to a T. Therefore, examples of probes designed to be complementary to the gene for sickle cell anemia have the following sequences:

```
3' GA GGA CAC CTY TTC AGA CG 5'
   GA GGA YAC CTC TTC AGA CG
   GA GGA CAY CTC TTC AGA CG
   GA GGA CAC YTC TTC AGA CG
Y = 2'-deoxy-3-deazauridine
```

Furthermore, based on the sequence disclosure in Kidd et al., *Nature,* 304:230, 1983, a probe of the present invention can be designed to hybridize to the complementary sequence in the gene containing the normal sequence for α1-antitrypsin. Also, a probe of the invention containing 2'-deoxy-3-deazauridine can be designed to hybridize to the corresponding gene sequence responsible for β1-antitrypsin deficiency. A segment of the normal gene for α1-antitrypsin has the following sequence:

```
            *
5' ACC ATC GAC GAG AAA GGG A 3'
3' TGG TAG CTG CTC TTT CCC T 5'
```

Probes of the invention that can be designed complementary to the normal gene segment have the following sequences:

```
3' TGG TAG CTG CTY TTT CCC T 5'
   TGG TAG YTG CTC TTT CCC T
   TGG TAG CTG YTC TTT CCC T
Y = 2'-deoxy-3-deazauridine
```

Probes of the invention that can be designed to be complementary to the sequence responsible for α1-antitrypsin deficiency, where the starred G in the normal gene sequence is changed to an A, have the following sequences:

```
3' TGG TAG CTG TTY TTT CCC T 5'
   TGG TAG YTG TTC TTT CCC T
Y = 2'-deoxy-3-deazauridine
```

Point mutations may arise from a single base substitution, insertion, or deletion in the DNA sequence of a single gene. Using a probe of the invention to detect such sequences would eliminate the dependencies on restriction enzyme recognition site alterations, which have a low probability of occurrence for any given point mutation. In addition, therapeutic uses for probes of the invention include insertion into various cells under conditions which allow them to hybridize to messenger RNA's (mRNA). The ability to hybridize to mRNA may allow for the inactivation of undesired mRNA's such as viral and oncogene mRNA. Not only can the probes of the invention be used to hybridize to mRNA in vivo, but the probes of the present invention may be used to hybridize, and therefore, inactivate mRNA during in vitro processes like in vitro translation.

DESCRIPTIONS OF THE PREFERRED EMBODIES

The following examples illustrate specific embodiments of the invention described herein. As would be apparent to skilled artisans, various changes and modifications are possible and are contemplated within the scope of the invention described.

The following structures listed in Table II are useful in the synthesis involved in the Examples.

TABLE 2

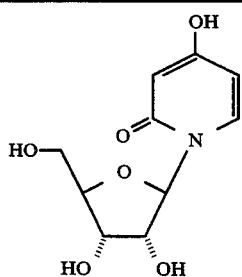

4-hydroxy-1-beta-D-erythro-pentofuranosyl-2(1H)-pyridone (1)

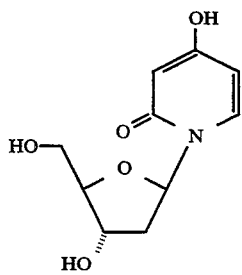

4-hydroxy-1-(2-deoxy-beta-D-erythro-pentofuranosyl)-2(1H)-pyridone (2)

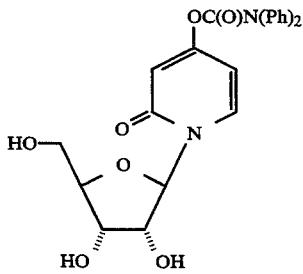

4-O-diphenylcarbamoyl-1-beta-D-erythro-pentofuranosyl-2(1H)-pyridone (3)

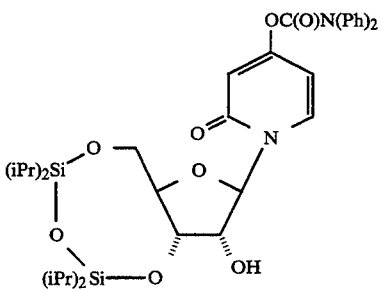

4-O-diphenylcarbamoyl-1-[3,5-O-[1,1,3,3-tetrakis-(1-methylethyl)-1,3-disiloxanediyl]-beta-D-erythro-pentofuranosyl]-2(1H)-pyridone (4)

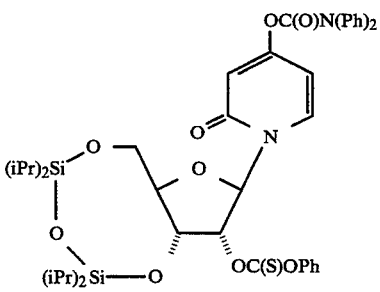

4-O-diphenylcarbamoyl-1-[2-O-(phenoxythioxomethyl)-3,5-O-[1,1,3,3-tetrakis(1-methylethyl)-1,3-disiloxanediyl]-beta-D-erythro-pentofuranosyl]-2(1H)-pyridone (5)

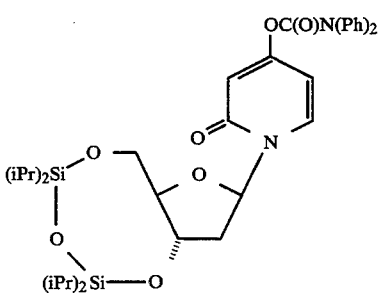

4-O-diphenylcarbamoyl-1-[2-deoxy-3,5-O-[1,1,3,3-tetrakis(1-methylethyl)-1,3-disiloxanediyl]-beta-D-erythro-pentofuranosyl]-2(1H)-pyridone (6)

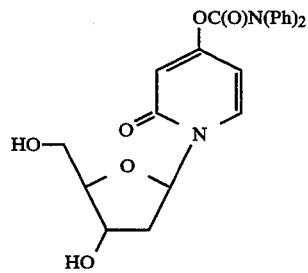

4-O-diphenylcarbamoyl-1-(2-deoxy-beta-D-erythro-pentofuranosyl)-2(1H)-pyridone (7)

TABLE 2-continued

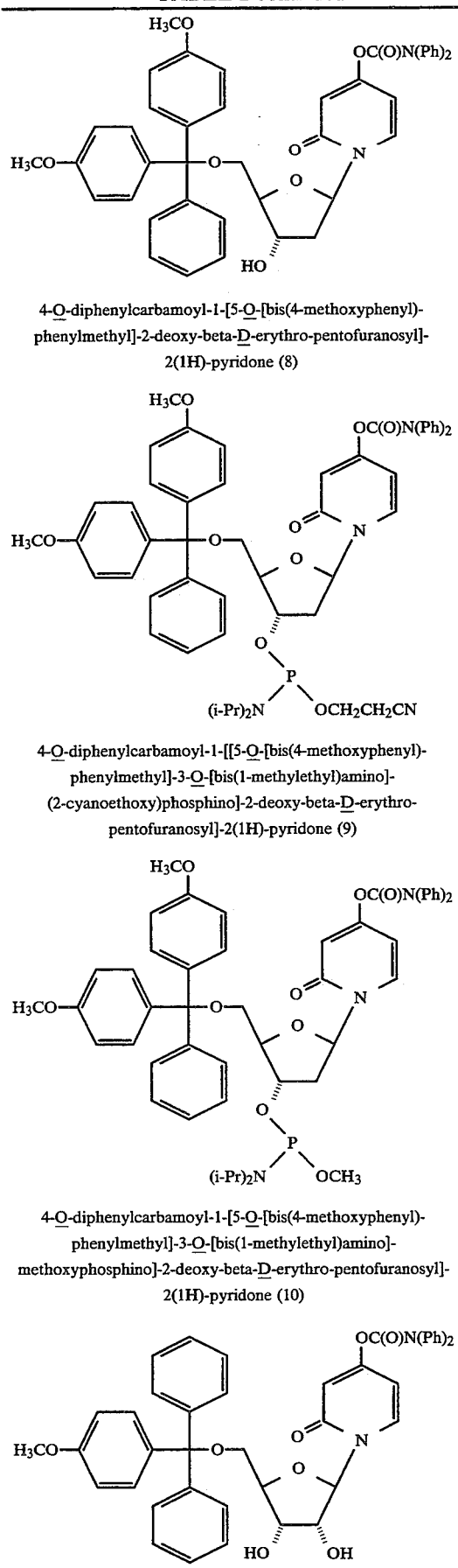

4-O-diphenylcarbamoyl-1-[5-O-[bis(4-methoxyphenyl)-
phenylmethyl]-2-deoxy-beta-D-erythro-pentofuranosyl]-
2(1H)-pyridone (8)

4-O-diphenylcarbamoyl-1-[[5-O-[bis(4-methoxyphenyl)-
phenylmethyl]-3-O-[bis(1-methylethyl)amino]-
(2-cyanoethoxy)phosphino]-2-deoxy-beta-D-erythro-
pentofuranosyl]-2(1H)-pyridone (9)

4-O-diphenylcarbamoyl-1-[5-O-[bis(4-methoxyphenyl)-
phenylmethyl]-3-O-[bis(1-methylethyl)amino]-
methoxyphosphino]-2-deoxy-beta-D-erythro-pentofuranosyl]-
2(1H)-pyridone (10)

TABLE 2-continued

4-O-diphenylcarbamoyl-1-[5-O-[(4-methoxyphenyl)diphenyl-
methyl]-beta-D-erythro-pentofuranosyl-2(1H)-pyridone (11)

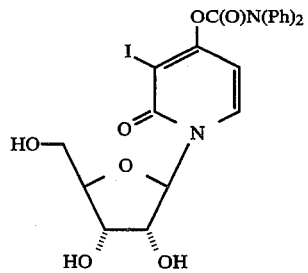

4-O-diphenylcarbamoyl-3-iodo-1-beta-D-erythro-
pentofuranosyl-2(1H)-pyridone (12)

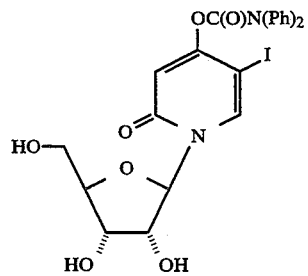

4-O-diphenylcarbamoyl-5-iodo-1-beta-D-erythro-
pentofuranosyl-2(1H)-pyridone (13)

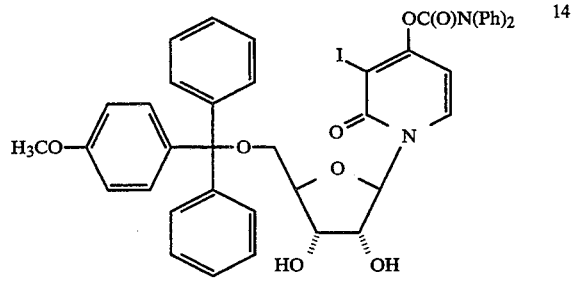

4-O-diphenylcarbamoyl-3-iodo-1-[5-O-[(4-methoxyphenyl)-
diphenylmethyl]-beta-D-erythro-pentofuranosyl]-2(1H)-
pyridone (14)

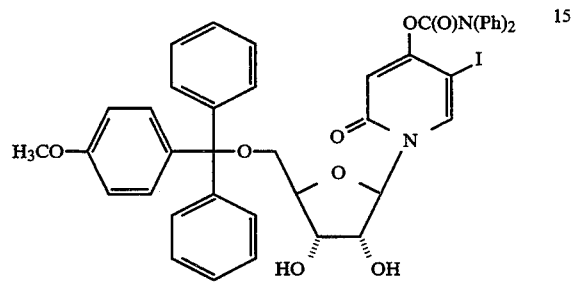

4-O-diphenylcarbamoyl-5-iodo-1-[5-O-[4-methoxyphenyl)-
diphenylmethyl]-beta-D-erythro-pentofuranosyl]-2(1H)-
pyridone (15)

TABLE 2-continued

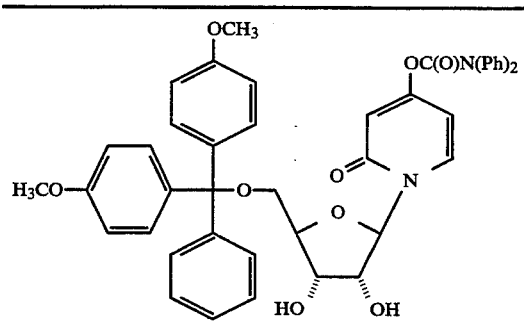

4-O-diphenylcarbamoyl-1-[5-O-[bis(4-methoxyphenyl)-phenylmethyl]-beta-D-erythro-pentofuranosyl]-2(1H)-pyridone (16)

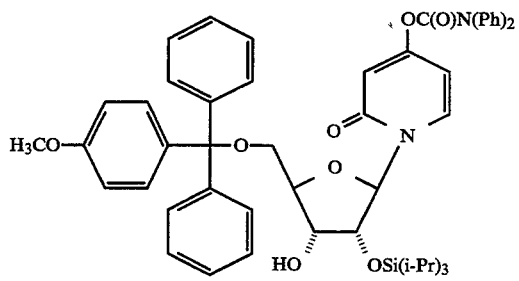

4-O-diphenylcarbamoyl-1-[[5-O-[(4-methoxyphenyl)-diphenylmethyl]-2-O-tris(1-methylethyl)silyl]-beta-D-erythro-pentofuranosyl]-1(2H)-pyridone (17)

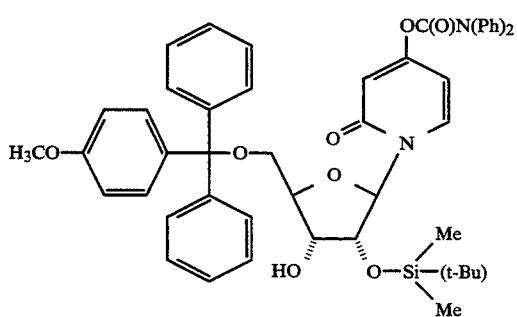

4-O-diphenylcarbamoyl-1-[[5-O-[(4-methoxyphenyl)-diphenylmethyl]-2-O-(1,1-methylethyl)dimethylsilyl]-beta-D-erythro-pentofuranosyl]-2(1H)-pyridone (18)

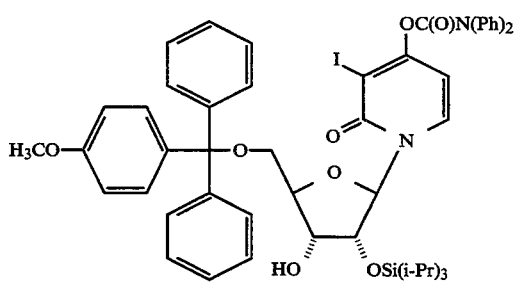

4-O-diphenylcarbamoyl-3-iodo-1-[[5-O-[(4-methoxyphenyl)-diphenylmethyl]-2-O-tris(1-methylethyl)silyl]-beta-D-erythro-pentofuranosyl]-2(1H)-pyridone (19)

TABLE 2-continued

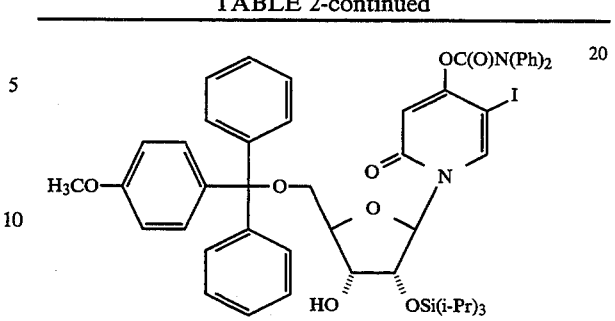

4-O-diphenylcarbamoyl-5-iodo-1-[[5-O-[(4-methoxyphenyl)-diphenylmethyl]-2-O-tris(1-methylethyl)silyl]-beta-D-erythro-pentofuranosyl]-2(1H)-pyridone (20)

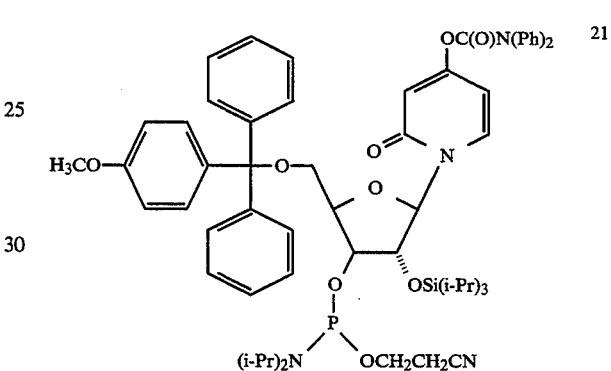

4-O-diphenylcarbamoyl-1-[[[5-O-[(4-methoxyphenyl)-diphenylmethyl]-3-O-[bis(1-methylethyl)amino]-(2-cyanoethyl)phosphino]-2-O-tris(1-methylethyl)silyl]-beta-D-erythro-pentofuranosyl]-2(1H)-pyridone (21)

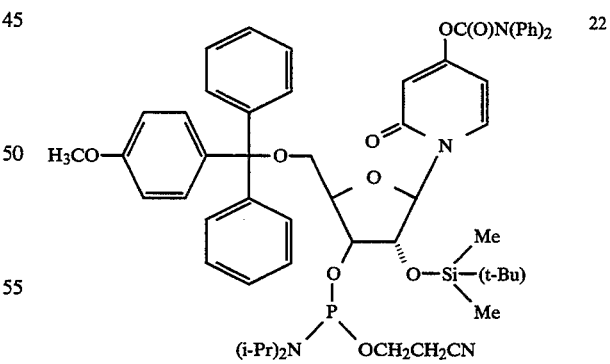

4-O-diphenylcarbamoyl-1-[[[5-O-[(4-methoxyphenyl)-diphenylmethyl]-3-O-[bis(1-methylethyl)amino]-(2-cyanoethyl)phosphino]-2-O-(1,1-methylethyl)-dimethylsilyl]-beta-D-erythro-pentofuranosyl]-2(1H)-pyridone (22)

TABLE 2-continued

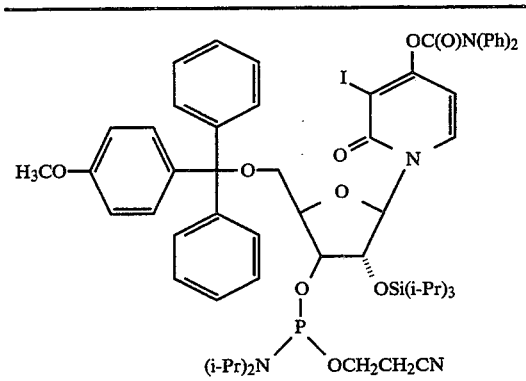

4-O-diphenylcarbamoyl-3-iodo-1-[[[5-O-[(4-methoxyphenyl)-diphenylmethyl]-3-O-[bis(1-methylethyl)amino](2-cyanoethyl)-phosphino]-2-O-tris(1-methylethyl)silyl]-beta-D-erythro-pentofuranosyl]-2(1H)-pyridone (23)

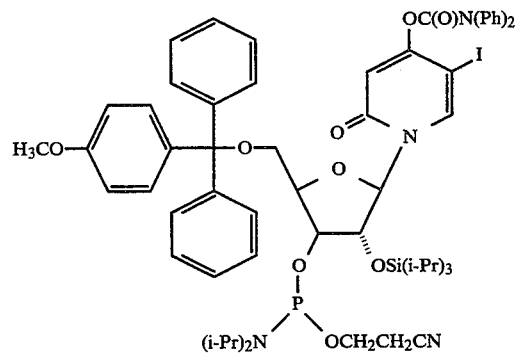

4-O-diphenylcarbamoyl-5-iodo-1-[[[5-O-[(4-methoxyphenyl)-diphenylmethyl]-3-O-[bis(1-methylethyl)amino](2-cyanoethyl)-phosphino]-2-O-tris(1-methylethyl)silyl]-beta-D-erythro-pentofuranosyl]-2(1H)-pyridone (24)

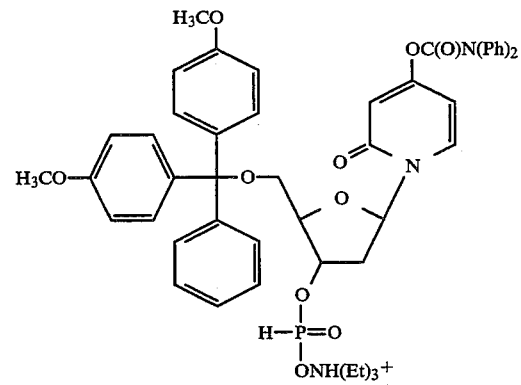

4-O-diphenylcarbamoyl-1-[[5-O-[bis(4-methoxyphenyl)-phenylmethyl]-3-O-(hydroxyphosphinyl)-2-deoxy]-beta-D-erythro-pentofuranosyl]-2(1H)-pyridone triethylammonium salt (25)

TABLE 2-continued

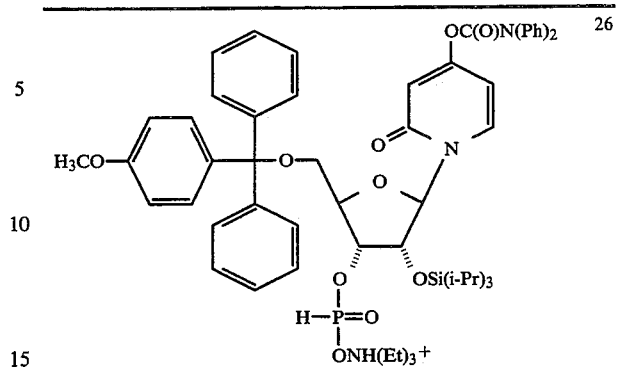

4-O-diphenylcarbamoyl-1-[[5-O-[(4-methoxyphenyl)-diphenylmethyl]-3-O-(hydroxyphosphinyl)-2-O-tris-(1-methylethyl)silyl]-beta-D-erythro-pentofuranosyl]-2(1H)-pyridone triethylammonium salt (26)

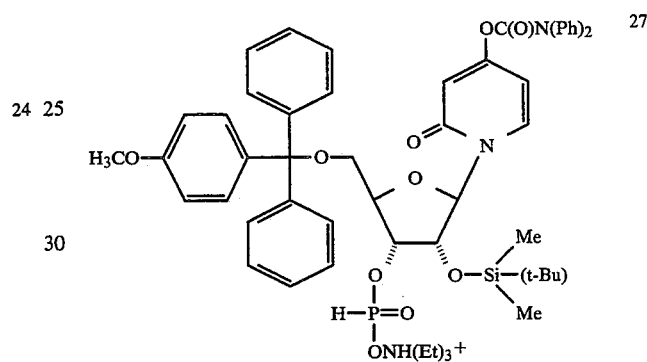

4-O-diphenylcarbamoyl-1-[[5-O-[(4-methoxyphenyl)-diphenylmethyl]-3-O-(hydroxyphosphinyl)-2-O-(1,1-dimethyl-ethyl)dimethylsilyl]-beta-D-erythro-pentofuranosyl]-2(1H)-pyridone triethylammonium salt (27)

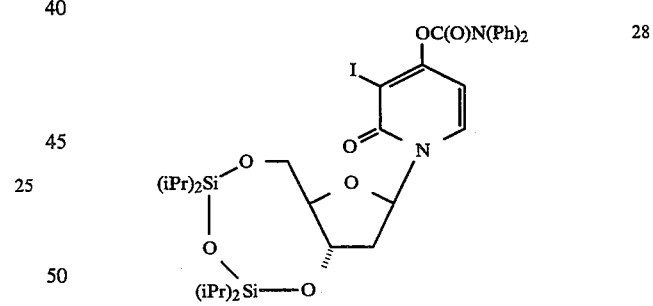

4-O-diphenylcarbamoyl-3-iodo-1-[2-deoxy-3,5-O-[1,1,3,3-tetrakis-(1-methylethyl)-1,3-disiloxanediyl]-beta-D-erythro-pentofuranosyl]-2(1H)-pyridone (28)

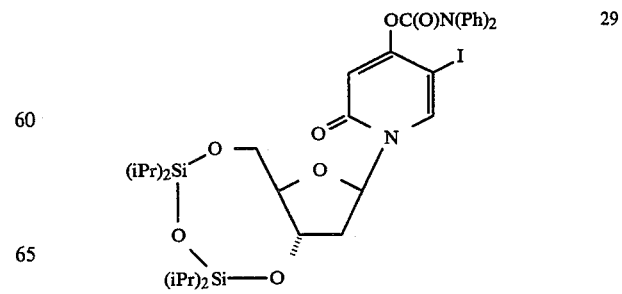

4-O-diphenylcarbamoyl-5-iodo-1-[2-deoxy-3,5-O-[1,1,3,3-tetrakis-

TABLE 2-continued (1-methylethyl)-1,3-disiloxanediyl]-beta-D-erythro-
pentofuranosyl]-2(1H)-pyridone (29)

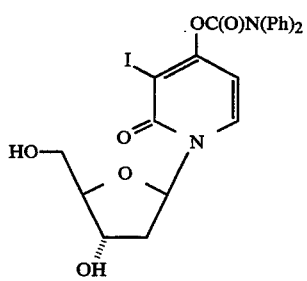

4-O-diphenylcarbamoyl-3-iodo-1-(2-deoxy-beta-
D-erythro-pentofuranosyl)-2(1H)-pyridone (30)

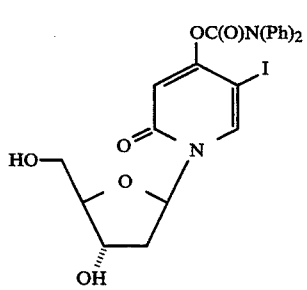

4-O-diphenylcarbamoyl-5-iodo-1-(2-deoxy-beta-
D-erythro-pentofuranosyl)-2(1H)-pyridone (31)

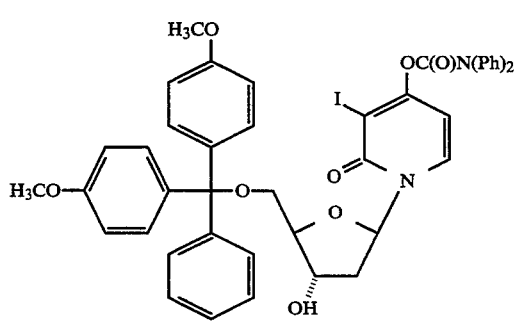

4-O-diphenylcarbamoyl-3-iodo-1-[5-O-[bis-
(4-methoxyphenyl)phenylmethyl]-2-deoxy-beta-
D-erythro-pentofuranosyl]-2(1H)-pyridone (32)

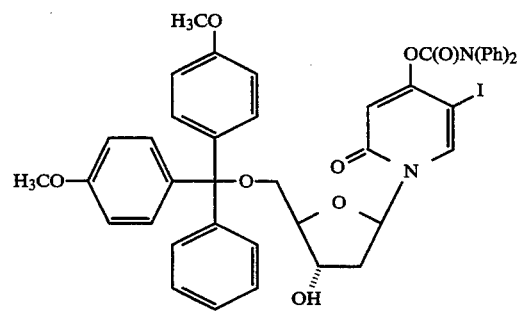

4-O-diphenylcarbamoyl-5-iodo-1-[5-O-[bis-
(4-methoxyphenyl)phenylmethyl]-2-deoxy-beta-D-erythro-
pentofuranosyl]-2(1H)-pyridone (33)

TABLE 2-continued

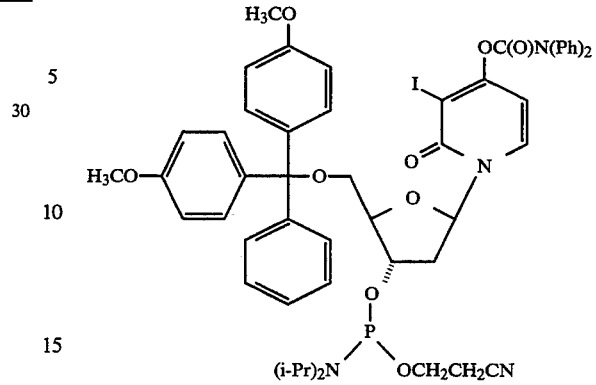

4-O-diphenylcarbamoyl-3-iodo-1-[5-O-[bis-
(4-methoxyphenyl)phenylmethyl]-[3-O-[bis(1-methyl-
ethyl)amino](2-cyanoethoxy)phosphino]-2-deoxy-
beta-D-erythro-pentofuranosyl]-2(1H)-pyridone (34)

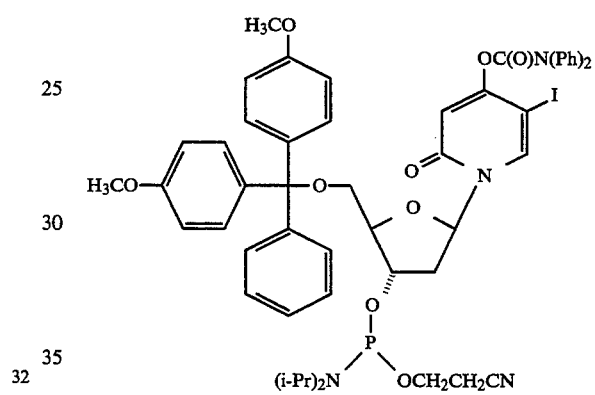

4-O-diphenylcarbamoyl-5-iodo-1-[5-O-[bis-
(4-methoxyphenyl)phenylmethyl]-[3-O-[bis(1-methyl-
ethyl)amino](2-cyanoethoxy)phosphino]-2-deoxy-
beta-D-erythro-pentofuranosyl]-2(1H)-pyridone (35)

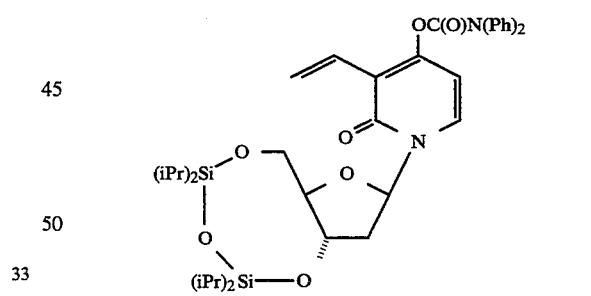

4-O-diphenylcarbamoyl-3-ethenyl-1[2-deoxy-
3,5-O-[1,1,3,3-tetrakis(1-methylethyl)-
1,3-disiloxanediyl]-beta-D-erythro-pentofuranosyl]-
2(1H)-pyridone (36)

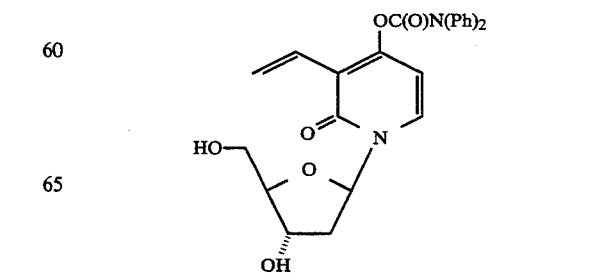

TABLE 2-continued

4-O-diphenylcarbamoyl-3-ethenyl-1(2-deoxy-beta-D-erythro-pentofuranosyl)-2(1H)-pyridone (37)

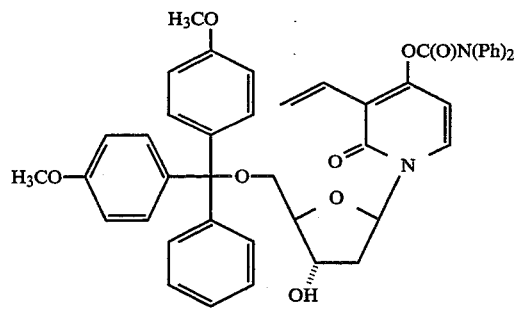

38

4-O-diphenylcarbamoyl-3-ethenyl-1-[5-O-[bis-(4-methoxyphenyl)phenylmethyl]-2-deoxy-beta-D-erythro-pentofuranosyl]-2(1H)-pyridone (38)

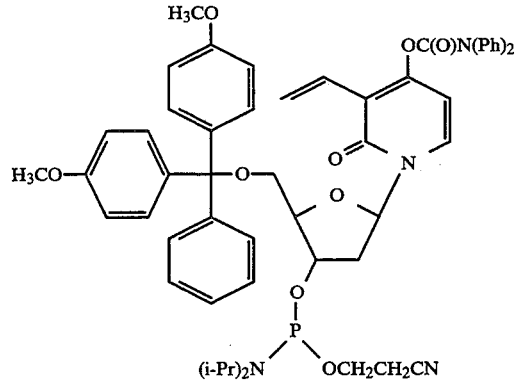

39

4-O-diphenylcarbamoyl-3-ethenyl-1-[5-O-[bis-(4-methoxyphenyl)phenylmethyl]-[3-O-[bis(1-methylethyl)-amino](2-cyanoethoxy)phosphino]-2-deoxy-beta-D-erythro-pentofuranosyl]-2(1H)-pyridone (39)

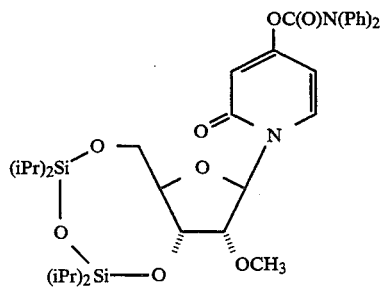

40

4-O-diphenylcarbamoyl-1-[[3,5-O-[1,1,3,3-tetrakis-(1-methylethyl)-1,3-disiloxanediyl]-2-O-methyl]-beta-D-erythro-pentofuranosyl]-2(1H)-pyridone (40)

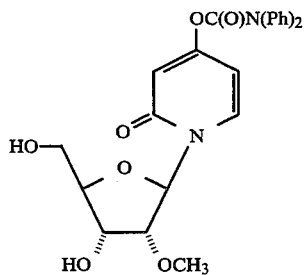

41

4-O-diphenylcarbamoyl-1-(2-O-methyl-beta-D-erythro-pentofuranosyl)-2(1H)-pyridone (41)

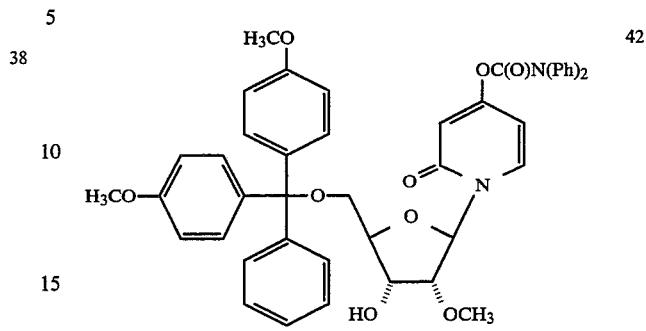

42

4-O-diphenylcarbamoyl-1-[5-O-[bis-(4-methoxyphenyl)phenylmethyl]-2-O-methyl-beta-D-erythro-pentofuranosyl]-2(1H)-pyridone (42)

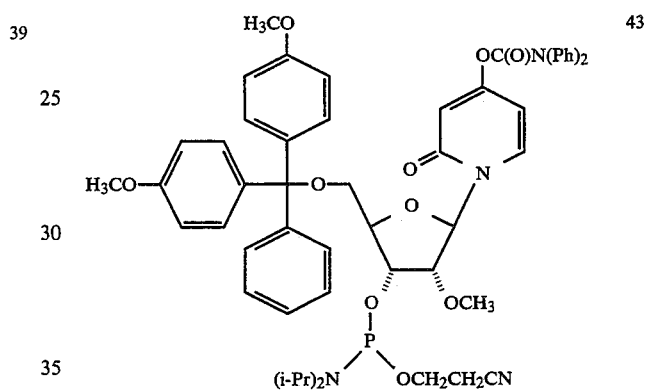

43

4-O-diphenylcarbamoyl-1-[5-O-[bis(4-methoxyphenyl)-phenylmethyl]-3-O-[bis(1-methylethyl)amino(2-cyano-ethoxy)phosphino]-2-O-methyl-beta-D-erythro-pentofuranosyl]-2(1H)-pyridone (43)

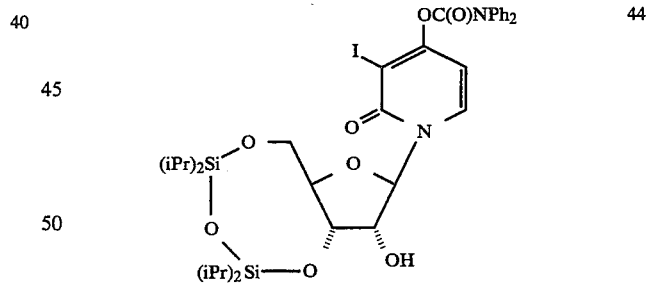

44

4-O-diphenylcarbamoyl-3-iodo-1-[3,5-O-[1,1,3,3-tetrakis-(1-methylethyl)-1,3-disiloxanediyl]-beta-D-erythro-pentofuranosyl]-2(1H)-pyridone (44)

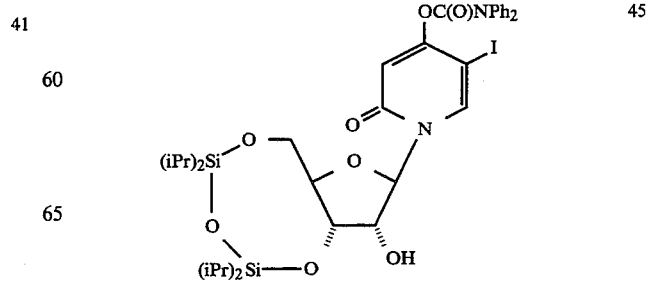

45

TABLE 2-continued

4-O-diphenylcarbamoyl-5-iodo-1-[3,5-O-[1,1,3,3-tetrakis-
(1-methylethyl)-1,3-disiloxanediyl]-beta-D-erythro-
pentofuranosyl]-2(1H)-pyridone (45)

EXAMPLE 1

4-hydroxy-1- beta-D-erythro-pentofuranosyl-2(1H)-pyridone (1), commonly called 3-deazauridine (Sigma, St. Louis, Mo.) is converted to the 4-O-diphenylcarbamoyl-1-beta-D-erythro-pentofuranosyl-2(1H)-pyridone (3), in the following manner. 15.0 gm. of 3-deazauridine are dried in a vacuum desiccator containing phosphorous pentoxide ($P_4O_{10}$) to obtain 14.7 gm. ( 6.04 $\times 10^{-2}$ mole). The dried starting uridine is placed in a round bottom flask and 140 mL acetonitrile ($CH_3CN$) and 50 mL dimethylformamide (DMF) added along with 16.1 mL (9.24$\times 10^{-2}$ mole) diisopropyl ethylamine. The mixture is stirred under argon and diphenylcarbamoyl chloride (22 gm., 9.50$\times 10^{-2}$ moles ) in 60 mLs $CH_3CN$ is added dropwise over about 30 minutes at room temperature. The reaction is stirred overnight resulting in a pale yellow solution. The volatiles are removed under reduced pressure on a rotary evaporator to obtain a thick syrup. The syrup is dissolved in toluene (50 mL) and concentrated under reduced pressure (this is repeated twice) and the residue is triturated with ethyl acetate (EtOAc) to obtain a white solid which is filtered, washed with EtOAc and ethanol (EtOH) and dried to give 16.8 gm. of pale yellow powder. The washings are concentrated and the residue purified by flash chromatography (Merck Silica) using EtOAc: methanol (MeOH) (3%): triethylamine ($Et_3N$) (0.5%). The fractions containing product are evaporated and triturated with EtOAc, filtered and dried to give another 6.5 gm. of desired product, 4-O-diphenylcarbamoyl-1-beta-D-erythro-pentofuranosyl-2(1H)-pyridone (3), (86% isolated yield). m.p. 167°-68° C.; Rf $CH_2Cl_2$: MeO 9:1)=0.4 $^1$HNMR, $\delta$(DMSO-$d_6$): 8.06 (d, 1H, J=7.66 Hz,H-6), 7.44–7.42 (m, 10H, aromatic), 6.29 (dd 1H, J=2.88, 7.66 Hz, H-5), 6.20 (d, 1H, J=5.49 Hz, H-1'), 5.99 (d, 1H, J=2.88 Hz, H-3), 5.42 (d, 1H, J=5.18 Hz, 2'-OH), 5.13 (t, 1H, J=5.05 Hz, 5'-OH), 5.03 (d, 1H, J=5.36 Hz, 3'-OH), 3.96 & 3.88 (m, 3H, H-2', 3' & 4'), 3.70 (m, 1H, H-5'), 3.60 (m, 1H, H-5"): mass spectrum (FAB) m/z (relative intensity) 439 (M+Li)+ (80), 307 (100), 196 (75); Elemental Analysis: calculated for $C_{23}H_{22}N_2O_7$: C, 63.01; H, 5.02; N, 6.54 Found C, 63.17; H, 5.15 N, 6.29.

To 15.0 gin. ( 0. 0343 mole ) of 4-O-diphenylcarbamoyl-1-beta-D-erythro-pentofuranosyl-2(1H)-pyridone (3), dissolved in 150 mL dry DMF (Aldrich) is added 30.1 mL (0.150 mole) diisopropylethylamine. The solution is stirred under an Argon atmosphere and 11.9 mL (11.9 gm, 0.0381 mole) dichlorotetraisopropylsiloxane dissolved in 50 mL dry DMF is added in dropwise fashion over about 1 hour. The reaction is carried out at room temperature. TLC (Merck 60 -p.254, 1:1 hexane: EtOAc ) shows good conversion to product after several hours. The volatiles are removed under vacuum and worked up by dissolving the residue in methylene chloride ($CH_2Cl_2$) and water. The organic layer is separated, washed with 0.5M hydrochloric acid (BCl), and aqueous sodium bicarbonate (saturated) and dried with anhydrous sodium sulphate. The oil obtained upon removal of solvent is purified by preparative liquid chromatography (Waters Prep 500, silica gel, 3:1 hexane: ethyl acetate) to obtain 16.5 gm. (71% isolated yield) of light yellow product, 4-O-diphenylcarbamol-1- [3,5-O-[1,1,3,3-tetrakis(1-methylethyl )-1, 3-disiloxanediyl]-beta-D-erythro-pentofuranosyl-2 (1H)-pyridone (4), RF 0.36 (EtOAC: hexane 1:1); $^1$H NMR, $\delta$ (CDCl$_3$): 7.78 (d, 1H, J=7.8 H-2 H-6, 7.4–7.26 (M, 10H, Aromatic) 6.31 (d, H, J=2.44 Hz, H-3), 6.20 (dd, 1H, J=7.8, 2.53 Hz, H-5), 4.32–3.99 (m, 5H, H-2', 3', 4', 5' & 5"), 3.03 (d, 1H, J=1.1 Hz 2'-OH), 1.1–0.96 (m, 28H, 2x Si-i-propyl); mass spectrum (FAB) m/z 687 (M+Li)+; HR FAB MS: Calculated for $C_{35}H_{48}N_2Si_2O_8Li$, 687.3109 - Found 687.3099.

To 6.5 gin. (9.5$\times 10^{-3}$ mole) 4-O-diphenylcarbamoyl-1-[3,5-O-[1,1,3,3-tetrakis(1-methylethyl) -1,3-disiloxanediyl]-beta-D-erythro-pentofuranosyl]-2(1H)-pyridone (4), dissolved in 65 mL $CH_2Cl_2$ is added 1.75 gm (1.43$\times 10^{-2}$ mole) 4-dimethylaminopyidine, and 1.45 mL (1.81 gm, 1.05$\times 10^{-2}$ mole) phenoxythionocarbonyl chloride. The reaction mixture is stirred overnight at room temperature under argon. The volatiles are removed under vacuum and the orange semi-solid residue taken up in EtOAc. The organic layer is washed with water, 0.25N HCl and saturated aqueous NaHCO$_3$. The organic layer is dried with magnesium sulphate (MgSO$_4$), filtered, and concentrated to about 25 mL. Purification is achieved by silica gel chromatography on a Waters Prep 500 using 3:1 hexane: EtOAc. A yellowish product is obtained which if carried forward at this stage does not reduce well. A second pass over silica gel is carried out to obtain 6.9 gm. of light yellow amorphous product (90% isolated yield), 4-O-diphenylcarbamoyl-1-[2-O-(phenoxythioxomethyl)-3,5-O-[1,1,3,3-tetrakis(1-methylethyl) -1,3-disiloxanediyl]-beta-D-erythro-pentofuranosyl]-2(1H)-pyridone (5). M.p. 117° C. (dcomp). RF 0.57 (EtOAc: Hexane 1:1); $^1$HNMR, $\delta$(CDCl$_3$): 7.79 (d, 1H, J=7.8 Hz, H-6), 7.43–7.11 (m, 15H, aromatic), 6.32 (d, 1H, J=2.44 Hz, H-3); 6.19 (dd, 1H, J=2.44, 7.8 Hz, H-5), 5.97 (d, 1H, J=4.69 Hz, H-1), 4.5 (dd, 1H, J=4.7, 9.4 Hz, H-3), 4.28 (m, 1H, H-4'), 4.15 (m, 1H, H-5'), 4.05 (m, 1H, H-5"), 1.55–0.96 (M, 28H, 2x-Si-(i-propyl)2); mass spectrum (FAB)m/z (relative intensity) 824 (M+Li)+(20), 664 (100), 307 (40); HR FAB MS: Calculated for $C_{42}H_{52}N_2Si_2SO_9Li$ 823.3092. Found 823.3084. Elemental analysis: calculated for $C_{42}H_{52}N_2Si_2SO_9$; C,61.76; H,6.37; N,3.43. Found C,61.82; H,6.37; N, 3.32.

To 6.0 gm. ( 7.3$\times 10^{-3}$ mole) 4-O-diphenylcarbamoyl-1-[2'-O-(phenoxythioxomethyl) -3',5'-O-[1,1,3,3-tetrakis(1-methylethyl)-1,3-disiloxanediyl]-beta-D-erythro-pentofuranosyl]-2(1H)-pyridone (5) in 75 mL toluene is added 2.94 mL tri-n-butyl-tin hydride (1.0 $\times 10^{-2}$ mole ) and 0.24 g AIBN (azobisisobutyronitrile, 1.5$\times 10^{-3}$ mole). The reaction mixture is stirred under argon atmosphere at 85° C. for 16 hours. The toluene is removed under reduced pressure and the residue purified by flash chromatography on silica gel using 3:1 EtOAc:hexane as eluent. Appropriate fractions are combined and dried under vacuum to give 4.1 gm 84% isolated yield of the desired product as a syrup 4-O-diphenylcarbamoyl-1-[2-deoxy-3,5-O-[1,1,3,3-tetrakis (1-methylethyl )-1,3-disiloxanediyl]-beta-D-erythro-pentofuranosyl]-2(1H)-pyridone (6), Rf 0.52 (EtOAc: Hexane 1:1); $^1$HNMR $\delta$(CDCl$_3$): 7.84 (d, 1H, J=7.83 Hz, H-5), 7.4–7.24 (m, 10H, Aromatic), 6.31 (d, 1H J=2.09 Hz, H-3), 6.22 (m, 2H, H-5, H-5'), 4.4 (m, H-3'), 4.14 (m, 1H, H-4'),4.05 (m, 1H, H-5'), 3.81 (m, 1H, H-5"), 2.60 (m, 1H, H-2'), 2.25 (m, 1H, H-2"), 1.09–0.98

(m, 28H, 2x-Si-(i-propyl)$_2$); mass spectrum (FAB) m/z (relative intensity) 672 (M+Li)$^+$ (80), 482 (10), 313 (100). HR FAB MS: Calculated for C$_{35}$H$_{48}$O$_7$N$_3$Si$_3$Li, 671.3160. Found 671.3171.

To 3.0 gm (4.5×10$^{-3}$ mole) 4-O-diphenylcarbamoyl-1-[2-deoxy-3,5-O-[1,1,3,3-tetrakis(1-methylethyl)-1,3-disiloxanediyl]-beta-D-erythro-pentofuranosyl]-2(1H)-pyridone (6), in 30 mL CH$_3$CN at 0° C. is added 0.62 gm (2.0×10$^{-3}$ mole ) tetrabutylammonium fluoride trihydrate (Aldrich, Milwaukee, Wis.) with stirring. The reaction mixture is stirred at 0° C. for 30 minutes, then stirred for 30 minutes at room temperature. Solvent is removed under reduced pressure and the desired product isolated by silica gel flash chromatography using 4:1 CH$_2$Cl$_2$:MeOH containing 0.5% Et$_3$N. A total of 1.5 gm. (79% isolated yield) of desired 4-O-diphenyl carbamoyl-1-(2-deoxy-beta-D-erythro-pentofuranosyl)-2(1H)-pyridone (7), is obtained. The product is crystallized from EtOAc; mp 147°-48° C. Rf 0.4 (CH$_2$Cl$_2$:MeOH 9:1) $^1$HNMR, $\delta$(DMSO-d6) 7.98 ( d, 1H, J=7.77 Hz, H-6), 7.43-7.3 (m, 10H, aromatic), 6.30 (m, 2H, H-5, H-6), 6.18 (d, 1H, J=2.56 Hz, H-3), 5.23 (d, 1H J=4.18 Hz, 2'-OH), 5.01 (t, 1H, 5'-OH), 4.20 (m, 1H, 3'-H), 3.84 ( m, 1H, H-4'), 3.6 ( m, 2H, H-5' & 5"), 2.25 (m, 1H, H-2'), 1.95 (m, 1H, H-2); mass spectrum FAB m/z (relative intensity) 423 (M+Li)$^+$ (70), 312 (90), 242 (100); Analysis calculated for: C$_{23}$H$_{22}$N$_2$O$_6$0.5H$_2$O: C, 65.03: H, 5.34 N, 6.49. Found: C, 65.04: H, 5.21; N, 6.57.

To 1.1 gm (2.61×10$^{-3}$ mole ) 4-O-diphenylcarbamoyl-1-(2-deoxy-beta-D-erythro-pentofuranosyl) -2 (1H)-pyridone (7), in 15 mL dry pyridine is added 1.3 gm (3.8×10$^{-3}$ mole) dimethoxyrtrityl chloride, 0.68 mL (3.9×10$^{-3}$ mole) diisopropylethylamine and 30 mg 4-N,N-dimethylaminopyridine (2.5×10$^{-4}$ mole). The reaction mixture is stirred at room temperature under argon for 4 hours. Volatiles are removed under reduced pressure and excess pyridine is removed by repeated (3×20 mL) distillation of toluene under reduced pressure. The residue is purified by silica gel flash chromatography using 2% MeOH in CH$_2$Cl$_2$ containing 0.5% triethylamine. 1.1 gm of a yellow amorphous solid is obtained which is rechromatographed (same solvent) to give 0.9 gm (1.44×10$^{-3}$ mole) desired product as a white amorphous material, 4-O-diphenylcarbamoyl-1-[5-O-[bis(4-methoxyphenyl)phenylmethyl]-2'-deoxy-beta-D-erythro-pentofuranosyl]-2(1H)pyridone (8). RF 0.56 (CH$_2$Cl$_2$:MeOH, 9:1); $^1$HNMR, $\delta$(CDCl$_3$): 7.92 (d, 1H, J=7.89 Hz, H-6), 7.42-7.22 (m, 19H, aromatic), 6.84 (2s, 4H, aromatic), 6.39 (dd, 1H, J=5.9 Hz, H-1'), 6.25 (d, 1H, J=2.52 Hz, H-3), 5.97 (dd, 1H, J=2.44, 7.89 Hz; H-5), 4.47 (m, 1H, H-4'), 4.03 (m, 1H, H-4'), 3.77 (s, 6H, 2-OCH$_3$), 3.5 (m, 1H, H-5'), 3.42 (m, 1H, H-5"), 2.60 (m, 1H, H-2'), 2.2 (m, 1H, H-2"); mass spectrum (FAB)m/z (relative intensity) 731 (m+Li)$^+$ (25), 427 (100); PIP, FAB MS; C$_{44}$H$_{40}$N$_2$O$_8$: 731.2945, found; 731.2939.

To 0.47 gm (6.43×10$^{-4}$ mole) 4-O-diphenylcarbamoyl-1-[5-O-[bis(4-methoxyphenyl)phenylmethyl]-2-deoxy-beta-D-erythro-pentofuranosyl]-2(1H )-pyridone (8), in 8 mL CH$_2$Cl$_2$ is added 0.45 mL (2.5×10 mole) N,N-diisopropylethylamine. 0.3 gm (1.27×10 mole) $\beta$-cyanoethyloxy-N,N-diisopropyl chlorophosphine (ABN) in 1 mL CH$_2$Cl$_2$ is added dropwise over about 15 minutes. The reaction mixture is stirred under argon atmosphere at room temperature for an additional hour. The solution is concentrated to dryness using a rotary evaporator, dissolved in EtOAc and washed with saturated aqueous NaHCO$_3$ (3×20 mL ), distilled water and dried with (MgSO$_4$). The yellow solution is evaporated to dryness and dried under vacuum to give 07.4 gm of viscous product that is dissolved in EtOAc and precipitated by the addition of hexane. The mixture is cooled, solvents decanted and the residue washed with cold hexane and dried under vacuum to give 0.55 gm (6.0×10$^{-4}$ mole, 79% isolated yield ) of 4-O-diphenylcarbamoyl-1- [[5-O-[bis ( 4-methoxyphenyl)phenylmethyl]-3-O-[bis (1-methylethyl)amino]-(2-cyanoethoxy)-phosphino]-2-deoxy-beta-D-erythro-pentofuranosyl]-2(1H)-pyridone (9), TLC conditions; Merck silica gel 60 p254, EtOAc: Hexane, 1:1; RF=0.27.$^1$HNMR, $\delta$(CDCl$_3$) 7.99, 7.92 (2d 1H, J=7.73 Hz, H-6), 7.42–7.22 (m, 19H aromatic), 6.84 (m, 4B, aromatic), 6.42 (dd, 1H, J=6.27 Hz, H-1), 6.26 (d, 1H, J=2.44 Hz,H-3), 5.89 (dd 1H, J =2.43, 7.8 Hz, H-5), 4.6 (m, 1H, H-3'), 4.15 (m, 1H, H-4'), 3.76 (s, 6H, 2x-OCHs), 3.74-3.35 (m, 4H, H-5', 5", 2x CH(Me)$_2$), 2.65 (m, 1H, H-2'), 2.6 (t, 2H, J=6.34 Hz, CH$_2$CN ), 2.4 ( T, 2H, J=6.3 Hz, CH2), 2.2 ( m, 1H, H-2"), 1.28-1.05 (m, 12H, 2x-N-CH (CH$_3$)$_2$); mass spectrum (FAB) m/z (relative intensity):931 (m+Li)$^+$ (100), 627 (15); HR FAB MS: calculated for C$_{53}$H$_{57}$N$_4$ O$_9$ PLi, 931.4023; Found 931.4015.

EXAMPLE 2

4-O-diphenylcarbamoyl-1-[5-O-[bis(4-methoxyphenyl)phenylmethyl]-3-O[bis(1-methylethyl)amino]-methoxyphosphino]-2-deoxy-beta-D-erythro-pentofuranosyl]-2(1H)-pyridone (10), is synthesized from 4-O-diphenyl-carbamoyl-1-[5-O-[bis(4-methoxyphenyl)phenylmethyl]-2-deoxy-beta-D-erythro-pentofuranosyl]-2(1H)-pyridone (8), and N,N-diisopropylmethylphosphonamidic chloride in substantial accordance with the teaching in Example 1. The yield of desired product after silica gel chromatography is 68%. 31-P NMR (CDCl$_3$, d, 149.2, 148.8 vs. 5% H$_3$PO$_4$).

EXAMPLE 3

4-O-diphenylcarbamoyl-1-beta-D-erythropentofuranosyl-2(1H)-pyridone (3), prepared in substantial accordance with the teaching of Example 1, can be converted to 4-O-diphenylcarbamoyl-1-5-O-[(4-methoxyphenyl)diphenylmethyl]-beta-D-erythro-pentofuranosyl]-2 (1H)-pyridone (11), in the following manner. To 15.0 gm (3.43×10$^{-2}$ mole) of 4-O-diphenylcarbamoyl-1-beta-D-erythro-pentofuranosyl-2(1H)-pyridone (3), dissolved in dry pyridine is added 10.5 mL (6×10$^{-2}$ mole ) diisopropylethylamine and 30 mg (2.5×10$^{-4}$ mole ) 4-N,N-dimethylaminopyridine. To this is added 11.7 gm (3.9×10$^{-2}$ mole) monomethoxytriphenylmethyl chloride. The reaction mixture is stirred at room temperature under argon atmosphere until complete. Volatiles are removed in vacuo and reduced pyridine is removed by repeated (3x) distillation of toluene under reduced pressure. The residue is purified by silica gel flash chromatography using a suitable solvent system made slightly basic with 0.5% triethylamine. In this manner the desired product, 4-O-diphenylcarbamoyl-1-5-O-[(4-methoxyphenyl)diphenylmethyl ]-beta-D-erythro-pentofuranosyl]-2(1H)-pyridone (11), can be obtained.

4-O-diphenylcarbamoyl-3-iodo-1-beta-D-erythropentofuranosyl-2(1H)-pyridone (12), and 4-O-diphenylcarbamoyl-5-iodo-1-beta-D-erythro-pentofuranosyl-2(1H)pyridone (13), can be converted to 4-O-diphenylcarbamoyl-3-iodo-1- [5-O-[(4-methoxyphenyl)diphenylmethyl]-beta-D-erythro-pentofuranosyl]-2(1H)-pyridone (14), and 4-O-diphenylcarbamoyl-5-iodo-1-[5-O-

[4-methoxyphenyl)diphenylmethyl]-beta-D-erythro-pentofuranosyl]-2(1H)-pyridone (15), respectively, in the same manner. 4-O-diphenylcarbamoyl-1-[5-O-[bis(4-methoxyphenylphenyl)methyl]-beta-D-erythro-pentofuranosyl]-2(1H)-pyridone (16), can be obtained in a similar manner by substituting dimethoxytriphenylmethyl chloride for monomethoxytriphenylmethyl chloride.

EXAMPLE 4

To 4.7 gm ($7.9 \times 10^{-3}$ mole) 4-O-diphenylcarbamoyl-1-[5-O-[(4-methoxyphenyl)diphenylmethyl]beta-D-erythro-pentofuranosyl]-2(1H)-pyridone (11) in anhydrous DMF under argon atmosphere is added 1.18 gm ($1.73 \times 10^{-3}$ mole) imidazole and 3.38 mLs ($1.58 \times 10^{-2}$ mole) triisopropylsilyl chloride while stirring. The reaction is allowed to proceed until complete, quenched with aqueous saturated $NaHCO_3$, and concentrated in vacuo. The resulting residue is co-evaporated with toluene, dissolved in $CH_2Cl_2$ and washed with water. The $CH_2Cl_2$ layer is dried with $MgSO_4$ lo (anhydrous) and concentrated in vacuo. The desired product, 4-O-diphenylcarbamoyl-1-[[5-O-[(4-methoxyphenyl)diphenylmethyl]-2-O-tris(1-methhylethyl)silyl]-beta-D-erythro-pentofuranosyl]-1(2H)-pyridone (17), can be obtained by silica gel chromatography in a fashion similar to that employed by N. Usman, K. K. Ogilvie, M. Y. Jiang, and R. J. Cedergren, *J. Am. Chem. Soc.*, 1987, 109, 7845–7854.

By substituting tert-butyldimethylsilyl chloride for triisopropylsilyl chloride, one can obtain 4-O-diphenylcarbamoyl-1-[[5-O-[(4-methoxyphenyl)diphenylmethyl]-2-O-(1,1-methylethyl)dimethylsilyl]-beta-D-erythro-pentofuranosyl]-2(1H)-pyridone (18). 4-O-diphenylcarbamoyl-3-iodo-1-[5-O-[(4-methoxyphenyl) diphenylmethyl]-beta-D-erythro-pentofuranosyl]-2(1H)-pyridone (14), and 4-O-diphenylcarbamoyl-5-iodo-1-[5-O-[4-methoxyphenyl)diphenylmethyl]-beta-D-erythropentofuranosyl]-2(1H)-pyridone (15), can be converted to 4-O-diphenylcarbamoyl-3-iodo-1-[[5-O-[(4-methoxyphenyl)diphenylmethyl]-2-O-tris(1-methylethyl)silyl]-beta-D-erythro-pentofuranosyl]-2(1H)-pyridone (19), and 4-O-diphenylcarbamoyl-5-iodo-1-[[5-O-[(4-methoxyphenyl)diphenylmethhyl]-2-O-tris(1-methylethyl) silyl]-beta-D-erythro-pentofuranosyl]-2(1H)-pyridone (20), respectively, in a similar manner.

EXAMPLE 5

To a stirred dry tetrahydrofuran (THP) solution of 7.0 mL ($4 \times 10^{-2}$ mole) diisopropylethylamine, 3.08 9m ($1.3 \times 10^{-2}$ mole) (N,N-diisopropyl)-$\beta$-cyanoethoxyphosphonamidic chloride and a catalytic amount (215 mg, $1.75 \times 10^{-3}$ mole) of 4-N,N-dimethylaminopyridine is added dropwise to a solution of 8.66 gm ($1 \times 10^{-2}$ mole) 4-O-diphenylcarbamoyl-1-[[-O-[(4-methoxyphenyl)diphenylmethyl]-2-O-tris(1-methylethyl)silyl]-beta-D-erythro-pentofuranosyl]-1(2H)-pyridone (1V), in dry THF. The reaction is allowed to go to completion and worked-up by adding EtOAc and washing with saturated aqueous $NaHCO_3$. The organic layer is dried and solvent removed in vacuo. The desired product, 4-O-diphenylcarbamoyl-1-[[[5-O-[(4-methoxyphenyl)diphenylmethyl]-3-O-[bis(1-methylethyl)amino](2-cyanoethyl) phosphino]-2-O-tris(1-methylethyl)silyl]-beta-D-erythropentofuranosyl]-2(1H)-pyridone (21), can be obtained in substantially pure form by silica gel flash chromatography.

In a similar fashion, 4-O-diphenylcarbamoyl-1- [[[5-O-[(4-methoxyphenyl)diphenylmethyl]-3-O-[bis (1-methylethyl)amino](2-cyanoethyl)phosphino]-2-O-(1,1-methylethyl)dimethylsilyl]-beta-D-erythro-pentofuranosyl]-2(1H)-pyridone (22), can be obtained by using 4-O-diphenylcarbamoyl-1-[[5-O-[(4-methoxyphenyl) diphenylmethyl]-2-O-(1,1-methylethyl)dimethylsily]-beta-D-erythro-pentofuranos]-2(1H)-pyridone (18). In the same manner, 4-O-diphenylcarbamoyl-3-iodo-1[[5-O-[(4-methoxyphenyl)diphenylmethyl]-2-O-tris(1-methylethyl)silyl]-beta-D-erythro-pentofuranosyl]-2(1H)pyridone (19), and 4-O-diphenylcarbamoyl-5-iodo-1[[5-O-[(4-methoxyphenyl)diphenylmethyl]-2-O-tris(1-methylethyl)silyl]-beta-D-pentofuranosyl]-2(1H)pyridone (20), can be converted to 4-O-diphenylcarbamoyl- 3-iodo-1-[[[5-O-[(4-methoxyphenyl)diphenylmethyl]-3-O-[bis(1-methylethyl)amino](2-cyanoethyl)phosphino]-2-O-tris(1-methylethyl)silyl]-beta-D-erythro-pentofuranosyl]-2(1H)-pyridone (23), and 4-O-diphenylcarbamoyl-5-iodo-1-[[[5-O-[(4-methoxyphenyl)diphenylmethyl]-3-O-[bis(1-methylethyl)amino](2-cyanoethyl)phosphino]-2-O-tris(1-methylethyl)silyl]-beta-D-erythro-pentofuranosyl]-2(1H)-pyridone (24 ), respectively.

EXAMPLE 6

4-O-diphenylcarbamoyl-1-[5-O-[bis(4-methoxyphenyl)phenylmethyl]-2-deoxy-beta-D-erythro-pentofuranosyl]-2(1H)-pyridone (8), can be converted to 4-O-diphenylcarbamoyl-1-[[5-O-[bis(4-methoxyphenyl)phenylmethyl]-3-O-(hydroxyphosphinyl)-2-deoxy]-beta-D-erythropentofuranosyl]-2(1H)-pyridone triethylammonium salt (25), in substantial accordance with the procedure of B. C. Froehler, P. G. Ng, and M. D. Matteucci, *Nuc. Acids Res.*, 14,5399–5407 (1986). Thus, to a stirred solution of phosphorous trichloride ($PCl_3$) (1.03 gm, $7.5 \times 10^{-3}$ mole) and N-methylmorpholine (7.59 gm, $7.5 \times 10^{-2}$ mole ) in 750 mL anhydrous $CH_2Cl_2$ is added 1,2,4-triazole (1.73 gm, $2.5 \times 10^{-2}$ mole) at room temperature. After 30 minutes the reaction mixture is cooled to 0° C. and 4-O-diphenylcarbamoyl-1-[5-O-[bis(4-methoxyphenyl)-phenylmethyl]-2-deoxy-beta-D-erythro-pentofuranosyl]-2(1H)-pyridone (8), (0.94 gm, $1.5 \times 10^{-3}$ mole) in 200 mL anhydrous $CH_2Cl_2$ is added dropwise over 20 minutes, stirred for 10 minutes, poured into 600 mL of 1.0M aqueous triethylammonium bicarbonate (TEAB, pH 8.5), shaken and separated. The aqueous phase is extracted with 200 mL $CH_2Cl_2$ and the combined organic phase dried over $Na_2SO_4$ and evaporated to a foam. The desired 4-O-diphenylcarbamoyl-1-[[5-O-[bis (4-methoxyphenyl)phenylmethyl]-3-O-(hydroxyphosphinyl)- 2-deoxy]-beta-D-erythro-pentofuranosyl]-2(1H )-pyridone triethylammonium salt (25), can be obtained by silica gel flash chromatography followed by TEAB extraction and evaporation. 4-O-diphenylcarbamoyl-1-[[5-O-[(4-methoxyphenyl)diphenylmethyl]-3-O-(hydroxyphosphinyl)-2-O-tris-(1-methylethyl)silyl]-beta-D-erythro-pentofuranosyl]-2(1H)-pyridone triethylammonium salt (26), and 4-O-diphenylcarbamoyl-1-[[5-O-[(4-methoxyphenyl)diphenylmethyl]-3-O-(hydroxyphosphinyl)-2-O(1,1-dimethylethyl)dimethylsilyl]-beta-D-erythropentofuranosyl]-2(1H)-pyridone triethyl ammonium salt (27), can be obtained in the same manner.

EXAMPLE 7

A mixture of 4-O-diphenylcarbamoyl-1-[2-deoxy-3,5-O-[1,1,3,3-tetrakis(1-methylethyl)-1,3-disiloxanediyl]-beta-D-erythro-pentofuranosyl]-2(1H )-pyridone, (6), (3.9 g, 0.0059 mol), N-iodosuccinimide (1.4 g, 0.0062 mol) in acetonitrile (40 mL) containing dichloroacetic acid (0.18 g, 0.0014 mol) is heated at 60° C. for 4 hours under argon atmosphere. The resulting dark brown solution is concentrated under reduced pressure and the residue dissolved in 125 mL of $CH_2Cl_2$. This solution is washed with saturated aqueous $NaHCO_3$ (3×25 mL) followed by water (2×50 mL), dried ($Na_2SO_4$) and concentrated in vacuo. The resulting dark brown residue is purified by silica gel flash chromatography using EtOAc:Hexane (1:4 v/v) as the eluent. The 3-iodo derivative is eluted first followed by the 5-iodo derivative. The fractions containing the 3-iodo derivative are combined, concentrated under reduced pressure and the residue crystallized from MeOH to give 4-O-diphenylcarbamoyl-3-iodo-1-[2-deoxy-3,5-O-[1,1,3,3-tetrakis(1-methylethyl)-1,3-disiloxanediyl]-beta-D-erythio-pentofuranosyl]-2(1S)-pyridone (28), (3.7 g, 80%) as shiny white flakes. m.p. 132°–33° C. $R_f$ 0.57 (EtOAc:Hexane 1:1). $^1$HNMR (300 MHz, $CDCl_3$) δ:7.9 (d, J=7.8 Hz,1,H6), 7.44–7.2 (m, 10, aromatic), 6.32 (d, J=7.8 Hz, 1,H5), 6.17 (d, J=6.73, 1, H1'), 4.39 (m, 1, H3'), 4.18 (m, 1, H5'), 4.04 (m, 1, H5''), 3.8 (m, 1, H4'), 2.59 (m, 1, H2'), 2.26 (m, 1, H2''), 1.1- 0.9 (m, 28.0[Si(iPr)$_2$]$_2$); FAB mass spectrum (m/z) 797 (M+Li), 439 (M+Li-sugar); Analysis calculated for $C_{35}H_{47}IN_2O_7$ $Si_2$:C, 53.16; H, 5.95; N, 3.54. Found: C,52.82; H, 5.95; N, 3.47. Fractions containing 4-O-diphenylcarbamoyl-5-iodo-1-[2-deoxy-3,5-O-[1,1,3,3-tetrakis (1-methylethyl)-1,3-disiloxanediyl]-beta-D-erythiopentofuranosyl]-2(1H)-pyridone (29) are combined, concentrated under reduced pressure and dried under high vacuum to give 0.25 g (5%), as an amorphous solid. $R_f$ 0.48 (EtOAc: Hexane 1:1). $^1$HNMR (300 MHz, $CDCl_3$) δ:8.01 (s, 1, H6), 7.4–7.2 (m, 10, aromatic), 6.52 (s, 1, H3), 6.13 (dxd, 1, H1'), 4.36 (m, 1, H3'), 4.15 (m, 1, H5'), 4.04 (m, 1, H5''), 3.8 (m, 1, H4')2.55 (m, 1, H2'), 2.25 (m, 1, H2''), 1.2–0.95 (m, 28 O[Si(i-Pr)$_2$]$_2$). FAB mass spectrum (m/z) 797 (M+Li), 439 (M+Li-sugar), HRFABMS observed (M+Li) 797. 2134 calculated for $C_{35}H_{47}IN_2O_7Si_2$ 797. 2127.

A mixture of 4-O-diphenylcarbamoyl-3-iodo-1[-2-deoxy-3,5-O-[1,1,3,3-tetrakis(1-methylethyl)-1,3-disiloxanediyl]-beta-D-erythio-pentofuranosyl]-2(1B)pyridone (28), (1 g, 0.0013 mL) and tetrabutylammonium fluoride trihydrate (0.25 g, 0.0008 mL) in acetonitrile (20 mL) is stirred at 0° C. for 30 minutes followed by stirring at room temperature for 30 minutes. The solution is concentrated under reduced pressure and the residue purified by silica gel flash chromatography using $CH_2Cl_2$-MeOH (4%) containing 0.5% $Et_3N$ as the eluent. Fractions containing 4-O-diphenylcarbamoyl-3-iodo-1-(2-deoxy-beta-D-erythio-pentofuranosyl)-2(1B)-pyridone (30), [indicated by TLC using $CH_2Cl_2$-MeOR(5%)]are combined, concentrated under reduced pressure and dried on a desiccator under vacuum to give 0.5 g (72%) of product. $R_f$ 0.49 ($C_2Cl_2$-MeOH 9:1) $^1$HNMR (300 MHz, DMSO-d$_6$) δ:8.07 (d, J=7.7 Hz, 1, H6), 7.47–7.3 (m, 10, aromatic) 6.48 (d, J=7.7 Hz, 1, H5), 6.26 (dxd, J=6.3 Hz, 1, H1'), 5.28 (d, J=4.2 Hz, 1, 2'-OH)5.08 (t, J=5.22 Hz, 1, 5'-OH), 4.23 (m, 1, H3'), 3.87 (m, 1, H4') 3.61 (m, 2, H5'×5''), 3.33 (s, 6, 2x-OCH$_3$), 2.29 (m, 1, H2'), 1.99 (m, 1, H2''); FAB mass spectrum (m/z) 549 (M+H), 433 (m-sugar); KRFABMS observed (M+Li) 555.0602, calculated for $C_{23}H_{21}N_2O_6$lLi 555.0604.

4-O-diphenylcarbamoyl-5-iodo-1-(2-deoxy-beta-D-erythio-pentofuranosyl)-2(1H)-pyridone (31), is obtained under similar reaction conditions as the 3-isomer, using tetraethylammonium fluoride, yield 63%. $R_f$0.47 ($CH_2Cl_2$-MeOH 9:1), $^1$HNMR (300 MHz, DMSO-d6) δ8.4 (s, 1, H6), 7.6–7.2 (m, 10, aromatic), 6.44 (s, 1, H3), 6.24 (dxd, J=6.3 Hz, 1, H1'), 5.24 (d, J=4.41 Hz, 1, 3'-OH), 5.14 (t, 1, 5'-OH), 4.23 (m, 1, H3'), 3.85 (m, 1, R4'), 3.59 (m, 2, H5'×5''), 2.49 (m, 1, H2 '), 2.02 (m, 1, H2''); FAB mass spectrum (m/z) 555 (M+Li), 439 (M+Li-sugar).

A mixture of 4-O-diphenylcarbamoyl-3-iodo-1-(2-deoxy-beta-D-erythro-pentofuranosyl)-2(1R )-pyridone (30), (0.22 g, 0.0006 mol), dimethoxytritylchloride (0.27 g, 0.0008 mol), dimethylaminopyridine (DMAP) (0.025 g) and diisopropylethylamine (0.14 mL, 0.0008 mol), in dry pyridine (5 mL) is stirred at room temperature for 6 hours and left overnight at 0'C. Pyridine is distilled under reduced pressure and the residue purified by silica gel flash chromatography using EtOAc-Hexane containing 0.5% EtaN. The appropriate fractions (visualized under UV lamp) are combined, concentrated under reduced pressure and the resulting residue dried under high vacuum to give 0.26 g (76%) of 4-O-diphenylcarbamoyl-3-iodo-1-[5-O-[bis(4-methoxyphenyl)phenylmethyl]-2-deoxy-beta-D-erythro-pentofuranosyl]-2(1)-pyridone (32), as an amorphous material (Homogenous on TLC). $R_f$=0.76 [$CH_2Cl_2$-MeOH (10%)]. $^1$HNMR ($CDCl_3$), δ:7.8 (d, J=7.7 Hz, 1, H6), 7.4–6.82 (m, 23, aromatic), 6.35 (d, J=7.7 Hz, H5), 6.2 (dxd, 1, H') 4.5 (m, 1, H3'), 4.05 (m, 1, H4'), 3.9 (m, 2, H5'×5'') 3.8 (s, 6, 2X-OCH$_3$), 2.50 (m, 1, H2'), 2.35 (m, 1, H2''); FAB mass spectrum (m/z): 857 (M+Li), 533 (M+Li-DMT); HRFABMS observed 857.1904, calculated for $C_{44}H_{39}IN_2O_8Li$ 857.1911.

4-O-diphenylcarbamoyl-5-iodo-1-[5-O-[bis (4-methoxyphenyl)phenylmethyl]-2-deoxy-beta-p-erythiopentofuranosyl]-2(1H)-pyridone (33), is prepared under similar reaction conditions. Yield 65%. $R_f$0.73 [$CH_2Cl_2$-MeOH (10%)]; $^1$HNMR (DMSO-d$_6$)δ:8.07 (s, 1, H6), 7.46–6.8 (m, 23 aromatic), 6.51 (s, 1, H3), 6.25 (dxd, 1, J=6.8 Hz, 1, H1'), 5.31 (d, J=4.35 Hz, 1, 3'-OH), 4.19 (m, 1, H3'), 3.98 (m, 1, H4'), 3.22 (m, 2, H5'×5''), 2.3 (m, 1, H2'), 2.1 (m, 1, H2''); FAB mass spectrum (m/z) 857 (M+Li), 553 (M+LiDMT).

To a chilled (ice bath) solution, 4-O-diphenylcarbamoyl-3-iodo-1-[5-O-[bis(4-methoxyphenyl)phenylmethyl]-2-deoxy-beta-D-erythio-pentofuranosyl]-2(1H)pyridone (32), (0.249, 0.00028 mol) in dichloromethane (5 mL ) containing diisopropylethylamine (0.1 mL, 0.00057 mol), is added dropwise a solution of p-cyanoethoxy-N,N-diisopropyrlamine chlorophosphine ( 0.1 g, 0.00042 mol), in dichloromethane (1 mL). The reaction mixture is stirred at room temperature for 2 hours. TLC (EtOAc) reveals completion of the reaction. The solution is concentrated to dryness, the residue dissolved in EtOAc (10 mL), and washed with 10% $NaHCO_3$ (3×10 mL), followed by water (3×10 mL ). The organic layer is dried over anhydrous $Na_2SO_4$, concentrated under reduced pressure and the resulting syrupy residue purified by silica gel flash chromatography using EtOAc-Hexane (1:1) as the eluent to give 0.2 g (63%) of 4-O-diphenylcarbamoyl-3-iodo-1-[5-O-[bis(4-methoxyphenyl)phenylmethyl]-[3-O-[bis(1-methylethyl)amino](2-cyanoethoxy)phosphino]-2- deoxy-beta-D-erythio-pentofuranosyl]-2(1H)-pyridone (34 ), as a white amorphous solid. $^1$H, NMR (300 MHz, CDCl$_3$) δ:8.20 (d, J=7.6 Hz, H6), 8.05 (d, J=7.6 Hz, H6), 7.46.8 (m, 23, aromatic), 6.35 (m, 1, H1'), 6.2×6.02 (d, J=7.6 Hz, 1, H5), 4.65×4.55 (m, 1, H3'), (4.15 (m, 1, H4'), 3.77 (2s, 6, 2x-OCH3), 3.85–3.3 (m, 4 H5'×5", -CH$_2$-O-P-) 2.75×2.25 (m, 2 H2'x H2"), 2.6×2.4 (2t, 2, -CH$_2$CN), 1.4–1.05 [(m, 14, N(i-Pr )$_2$]; FAB mass spectrum (m/z) 1057 (M+Li), 753 (M+Li-DMT); HIR-FABMS: observed 1057.2999, calculated for C$_{53}$H$_{56}$IN$_4$O$_9$ PLi 1057.2990.

4-O-diphenylcarbamoyl-5-iodo-1-[5-O-[bis (4-methoxyphenyl)phenylmethyl]-[3-O-[bis(1-methylethyl)amino](2-cyanoethoxy)phosphino]-2'-deoxy]-beta-D-erythio-pentofuranosyl]-2(1H)-pyridone (35) is prepared as described for the 3-iodo derivative. Yield 74%; $^1$HNMR (CDCl$_3$) δ:8.19×8.15 (2s, 1, H6), 7.5–6.8 (m, 23, aromatic), 6.51 (s, 1, 3H), 6.37 (d×d, 1, H1'), 4.5 (m, 1, H3') 4.19 (m, 1, H4'), 3.78 (2s, 6, 2–2.15 (m, 2, H2'×H2"), 2.6×2.4 (2t, 2, -CH$_2$CN) 1.35–1.05 [m, 14-N (i-Pr)$_2$]. FAB mass spectrum (m/z) 1057 (M+Li), 753 (M+Li-DMT), HRFABMS observed 1057. 3035, calculated for C$_{53}$H$_{50}$OIN$_4$O$_9$ P 1057.2990.

EXAMPLE 8

A mixture of 4-O-diphenylcarbamoyl-3-iodo-1-[2-deoxy-3,5-O-[1,1,3,3-tetrakis(1-methylethyl)-1,3-disiloxanediyl]-beta-D-erythro-pentofuranosyl]-2(1H)-pyridone (28), (1.2 g, 0.0015 mol), vinyl tri-n-butyltin (0.8 mL, 0.0027 mol ) and palladium chloride bistriphenylphosphine (0.1 g) in dry acetonitrile (20 mL) is heated at 60° C. for 16 hours, under argon atmosphere. The solution is concentrated under reduced pressure and excess vinyl tri-n-butyltin is removed by repeated (3 times) distillation with DMF. The resulting viscous oil is dissolved in ethylacetate (15 mL) filtered through celite and the filtrate concentrated to give a syrupy residue. This residue is purified by flash chromatography using EtOAc-Hexane (1:4) as the eluent. The fractions containing the desired product (visualized under UV) are combined, concentrated under reduced pressure arid the resulting residue dried under high vacuum in a desicator to give 0.85 g (82%) of 4-O-diphenylcarbamoyl-3-ethenyl-1[2-deoxy-3,5-O-[1,1,3,3-tetrakis(1-methylethyl)-1,3-disiloxanediyl]-beta-D-erythro-pentofuranosyl]-2(1H)-pyridone (36), as a pale yellow amorphous material. R$_f$=0.63 (EtOAc-Hexane 1:1); $^1$HNMR (300 MHz, CDCl$_3$) δ:7.79 (d, J=7.69 Hz, 1, H6), 7.42–7.2 (m, 10, aromatic), 6.45 (dxd, J=17.7 Hz & 11.85 Hz, 1, $\overline{CH}$=CH$_2$) 6.35 (d, J=7.69 Hz, Z, H5), 6.2 (m, 2, H1'×$\overline{CH}$=CH$_2$), 5.38 (dxd, J=2.5×11.8 Hz); 4.39 (m, 1, H3'), 4.2 (m, 2, H5'×5"), 3.8 (m, 1, H4'), 2.6 (m, 1, H2'), 2.26 (m, 1, H2"), 1.15–0.85 (m, 28, O[Si-(i-Pr)$_2$]$_2$; FAB mass spectrum (m/z) 697 (M+Li), 339 (M+Li-sugar); HRFABMS observed (M+Li) 697.3321, calculated for C$_{37}$H$_{50}$N$_2$O$_7$ Si$_2$Li 697.3317.

To a chilled (ice bath) solution of 4-O-diphenylcarbamoyl-3-ethenyl-1[2-deoxy-3,5-O-[1,1,3,3-tetrakis (1-methylethyl)-1,3-disiloxanediyl]-beta-D-erythio-pentofuranosyl]-2(1H)-pyridone (36) (0.3 g, 0.00063 mol) in acetonitrile (5 mL) is added tetraethylammonium fluoride (0. 035 g, 0.0002 mol). The reaction mixture is stirred at 0° C. for 30 minutes and at room temperature for 1 hour. During this period, desilyation is complete as revealed by TLC of the reaction mixture. The solution is concentrated under reduced pressure and the residue purified by flash Chromatography using CH$_2$Cl$_2$-MeOH (5%) containing 0.5% Et$_3$N to give 0.18 g (94%) of 4-O-diphenylcarbamoyl-3-ethenyl-1(2-deoxy-beta-D-erythio-pentofuranosyl)-2(1H)-pyridone (37). R$_f$=0.26 (CH$_2$Cl$_2$-MeOH, 5%); $^1$HNMR (300 MHz, DMSO-d$_6$) δ:7.98 (d, J=7.70 Hz, H6), 7.55–7.2 (m, 10, aromatic), 6.5 (m, 2, H5 & CH=CH$_2$), 6.49 (d: J=7.7 Hz, 1, H5), 6.39 (dxd, J=6.4 Hz, 1, H1'), 5.35 (dxd, 1, J=3.01 Hz, 11.9 Hz), 5.24 (d, 1, J=4.25 Hz, 2'-OH), 5.04 (t, 1, J=5.14 Hz, 5'-OH), 4.23 (m, 1, H3'), 3.86 (m, 1, H4'), 3.62 (m, 2, H5'×5"), 2.35 (m, 1, H2'), 2.00 (m, 1, H2"), FAB mass spectrum (m/z) 4.49 (M+H), 333; HRFABMS observed (M+Li) 455.1795 calculated for C$_{25}$H$_{24}$N$_2$O$_6$Li 455.1794.

A mixture of 4-O-diphenylcarbamoyl-3-ethenyl-1(2-deoxy-beta-D-erythio-pentofuranosyl)-2(1H)-pyridone (37), (0.1 g, 0.00022 mol), dimethoxytritylchloride (0.11 g, 0.00032 mol) and diisopropylethylamine (0.08 mL, 0.00046 mol) in anhydrous pyridine (3 mL) is stirred for 24 hours at room temperature under argon atmosphere. Pyridine is distilled off under reduced pressure and this residue purified by flash chromatography using EtOAc-Hexane (1:1) containing 0.5% Et$_3$N. Fractions containing the desired product (visualized under UV lamp) are combined, concentrated and this residue dried in a dessicator under high vacuum to afford 4-O-diphenylcarbamoyl-3-ethenyl-1[5-O-[bis(4-methoxyphenyl)phenylmethyl]-2-deoxy-beta D-erythro-pentofuranosyl]-2(1H)-pyridone (38), (0.13 g, 78%) as white amorphous material. R$_f$0.6 [CH$_2$Cl$_2$-MeOH (5%)]. $^1$HNMR (DMSO-d6) 7.82 (d, J=7.7 Hz, 1, H6), 7.466.8 (m, 23, aromatic) 6.5 (dxd, 1, —CH=CH$_2$), 6.3 (m, 3, H1 ', H5'×—CH=CH$_2$), 5.35 (m, 2, 2 '—OH-X—CH=CH$_2$), 4.27 (m, 1, H3'), 3.99 (m, 1, H4'), 3.72 (s, 6, 2x-OCH$_3$), 3.27 (m, 2, H5'×H5"), 2.4 (m, 1, H2'), 2.05 (m, 1, H2"); FAB mass spectrum (m/z): 757 (M+Li), 453.

To an ice cooled solution of 4-O-diphenyl-carbamoyl-3-ethenyl-1-[5-O-[bis(4-methoxyphenyl)phenylmethyl]-2-deoxy-beta-D-erythio-pentofuranosyl]-2(1H)pyridone (38), (0.11 g, 0.00015 mol) in dry dichloromethane (5 mL) containing diisopropylamine (0.05 mL, 0.00029 mol), is added dropwise a solution of N,N,-diisopropylamine-β-cyanoethoxychlorophosphine (0.052 g, 0.0002 mol) in dichloromethane (1 mL). The resulting mixture is stirred at 0° C. for 1 hour and at room temperature for 3 hours. TLC (EtOAC) revealed complete conversion to the product. The reaction mixture is concentrated under reduced pressure, the residue is dissolved in ethyl acetate (10 mL) and washed with 10% NaCO$_3$ (2×10 mL) followed by water (2×10 mL). The organic layer is dried (Na$_2$SO$_4$) and concentrated under reduced pressure to give a syrupy material. This syrupy material is purified by flash chromatography using EtOAc containing 0.5% Et$_3$N. The fractions containing 4-O-diphenylcarbamoyl-3-ethenyl-1[5-O-[bis(4-methoxyphenyl)phenylmethyl]-3-O-[bis (1-methylethyl)amino](2-cyanoethoxy)phosphino]-2-deoxy-beta-D-erythio-pentofuranosyl]-2(1H)-pyridone (39) are pooled, concentrated and dried in a desicator under vacuum to afford (0.13 g, 87%) as a white amorphous material. $^1$HNMR (CDCl$_3$) δ:7.93×7.8 (2d, J=7.7 Hz, 1, H6), 17.43 6.8 (m, 23, aromatic) 6.556.3 (m, 2, H1'×$\overline{CH}$=CH$_2$), 6.25 (m, 2, H5'×CH=CH$_2$), 5.35 (m, 1, —$\overline{CH}$=CH2), 4.50 (m, 1, H3'), 4.20 (m, 1, H4'), 3.76 (s, 6, 2x-OCH$_3$), 3.45 [m, 4, H5'×5"&-N-[CH(CH$_3$)$_2$]$_2$, 2.60×2.40 (2(—5,—CH-2—CH$_2$CN×H2'), 2.25 (m, 1, H2"), 1.35–1.0 [m, 12,-N-[CH(CH$_3$)$_2$[$_2$; FAB mass spectrum (m/z): 957 (M+Li), 733 & 653.

EXAMPLE 9

To 5.0 gm (7.3×10$^{-3}$ mole) 4-O-diphenylcarbamoyl-1-[3,5-O-[1,1,3,3-tetrakis(1-methylethyl)-1,3-disiloxanediyl]-beta-D-erythro-pentofuranosyl]-2(1H)-pyridone (4), in 30 mLs dry DMF can be added 0.24 gm (1×10$^{-2}$ mole) NaH while stirring. To this is added 1.26 gm (1×10$^{-2}$ mole) dimethyl sulfate. The reaction mixture is kept under argon until complete and then volatiles are removed under reduced pressure. The residue is taken up in EtOAc and the organic layer washed with saturated aqueous NaHCO$_3$ and distilled water, then dried (MgSO$_4$), filtered and solvent removed. Purification by silica gel chromatography can be used to give the desired product, 4-O-diphenylcarbamoyl-1-[[3,5-O-[1,1,3,3-tetrakis(1-methylethyl )-1,3-disiloxanediyl]-2'-O-methyl]-beta-D-erythro-pentofuranosyl]-2(1H)-pyridone (40). To 3.1 gm(4.5×10$^{-2}$ mole ) 4-O-diphenylcarbamoyl-1-[[3,5-O-[1,1,3,3-tetrakis(1-methylethyl)-1,3-disiloxanediyl]-2-O-methyl]-beta-D-erythio-pentofuranosyl]-2(1H)pyridone (40) in 30 mL CH$_3$CN at 0° C. is added 0.65 gm (2.0×10$^{-3}$ mole) tetraethylammonium fluoride trihydrate (Aldrich, Milwaukee, Wis.) while stirring. The reaction mixture is kept at 0° C. for 30 minutes, warmed to room temperature and kept at room temperature for 30 minutes. Solvent is removed under reduced pressure and the desired product can be isolated by silica gel flash chromatography to give 4-O-diphenylcarbamoyl-1(2-O-methyl-beta-D-erythio-pentofuranosyl)-2(1H)pyridone (41). To 1.4 gm (3.2×10$^{-3}$ mole) 4-O-diphenylcarbamoyl-1-(2'-O-methyl-beta-D-erythropentofuranosyl)-2(1H)-pyridone (41), in 15 mL dry pyridine is added 1.3 gm (3.95×10$^{-3}$ mole) diisopropylethylamine and 30 mg 4-N,N-dimethylaminopyridine (2.5×10$^{-4}$ mole) and 1.2 gm (3.5×10$^{-3}$ mole) dimethoxy tritylchloride. The reaction mixture is stirred at room temperature for 4 hours or until the reaction is substantially complete. Volatiles are removed and excess pyridine is removed by repeated (3×20 mL) distillation of toluene under reduced pressure. The residue is purified by silica gel chromatography and 4-O-diphenylcarbamoyl-1 -[5-O-[bis-(4-methoxyphenyl)phenylmethyl]-2'-O-methyl-beta-D-erythro-pentofuranosyl]-2(1H)-pyridone (42), can be obtained. To 0.55 gm (7.3×10$^{-4}$ mole) 4-O-diphenylcarbamoyl-1-[5'-O-[bis-(4-methoxyphenyl)phenylmethyl]-2'-O-methyl-beta-D-erythio-pentofuranosyl]-2(1H)pyridone (42), in CH$_2$Cl$_2$ is added 0.45 mL (2.5×10$^{-3}$ mole) N,N-diisopropylethylamine. To this is added, dropwise over about 15 minutes 0.19 gm (8.0×10$^{-4}$ mole) p-cyanoethyloxy-N,N-diisopropyl chlorophosphine (American Bionetics, Inc., Hayward, Calif.) in 5 mL CH$_2$Cl$_2$. The reaction mixture is stirred and kept under an argon atmosphere at room temperature for an additional hour. The solution is concentrated to dryness under vacuum using a rotary evaporator and the residue taken up in EtOAc, washed with saturated aqueous NaHCO$_3$ (3×20 mL ) and distilled water, then dried (MgSO$_4$). The solution is concentrated to dryness and dried under vacuum to give a product which can be isolated by taking it up in EtOAc and precipitating with hexane to give substantially pure 4-O-diphenylcarbamoyl-1-[5-O-[bis(4-methoxyphenyl)phenylmethyl]-3-O-[bis(1-methylethyl)amino(2-cyanoethoxy)phosphino]-2-O-methyl-beta-D-erythro-pentofuranosyl]-2(1H)-pyridone (43).

EXAMPLE 10

A mixture of 4-O-diphenylcarbamoyl-1-[3,5-O-[1,1,3,3-tetrakis(1-methylethyl )-1,3-disiloxanediyl]-beta-D-erythio-pentofuranosyl]-2(1H)-pyridone (4), (6.8 gm, 1×10$^{-2}$ mole), N-iodosuccinimide (2.7 gm, 1.2×10$^{-2}$ mole) in dry DMF containing dichloroacetic acid (0.36 gm, 2.8×10$^{-3}$ mole) is heated at 60° C. under argon atmosphere until the reaction is complete. The resulting mixture is concentrated in vacuo and the residue can be purified by silica gel flash chromatography to obtain as a major product 4-O-diphenylcarbamoyl-3-iodo-1-[3,5-O-[1,1,3,3-tetrakis(1-methylethyl)-1,3-disiloxanediyl]-beta-D-erythio-pentofuranosyl]-2(1H)-pyridone (44) and as a minor product 4-O-diphenylcarbamoyl-5-iodo-1-[3,5-O-[1,1,3,3-tetrakis (1-methylethyl)-1,3-disiloxanediyl]-beta-D-erythio-pentofuranosyl]-2(1H)-pyridone (45).

EXAMPLE 11

A mixture of 3.7 gm (4.6×10$^{-3}$ mole) of 4-O-diphenylcarbamoyl-3-iodo-1-[3,5-O-[1,1,3,3-tetrakis(1-methylethyl)-1,3-disiloxanediyl]-beta-D-erythiopentofuranosyl]-2(1H)-pyridone (44), and 0.88 gms (2.8×10$^{-3}$ mole) tetrabutylammonium fluoride trihydrate in acetonitrile is stirred at 0° C. for 30 minutes followed by stirring at room temperature for 30 minutes. The solution is concentrated in vacuo and the residue can be purified by silica gel flash chromatography to obtain 4-O-diphenylcarbamoyl-3-iodo-1-beta-D-erythro-pentofuranosyl-2(1H)-pyridone (12).

In a similar fashion, the 5-iodo isomer, 4-O-diphenylcarbamoyl-5-iodo-1-beta-D-erythio-pentofuranosyl-2(1H)-pyridone (13) can be obtained from 4-O-diphenylcarbamoyl-5-iodo-1 -[3,5-O-[1,1,3,3-tetrakis (1-methylethyl)-1,3-disiloxanediyl]-beta-D-erythiopentofuranosyl]-2(1H)-pyridone (45).

EXAMPLE 12

All DNA oligonucleotides of the invention are synthesized on an ABI 380B synthesizer (Applied Biosystems, Inc., Foster City, Calif.) on a 1 micromole scale. Purification is achieved by polyacrylamide gel electrophoresis (PAGE). Oligonucleotides are labelled at their 5' end by transfer of $^{32}$P phosphate from gamma-$^{32}$P-ATP using T4 polynucleotide kinase as described in T. Maniatis, E. F. Fritsch, and J. Sambrook, "Molecular Cloning", Cold Spring Harbor Laboratory, (1982). Radiolabelled probe is separated from the reaction mixture by Sephadex G-50 chromatograph (eluted with water). About 1×10$^6$ cpm/filter of labelled probe is included in the hybridization solution. After overnight hybridization, blots are washed in 6×SSC (Standard Saline Citrate) at the appropriate temperature for 5 minutes. Autoradiograms are obtained using Kodak XAR-5 film with one intensifying screen (24 hours).

EXAMPLE 13

The 0.8 Kb DNA fragment encoding the small subunit of soybean ribulose-1, 5-bisphosphate (RuBP) carboxylase (S. C. Berry-Low et al., *J. Mol. and Applied Gen.*, 1:483 (1982)) is obtained from plasmid pSRS 0.8 using the following conditions. 6.8 uL (400 ug) of pSRS 0.8 plasmid solution is combined with 8 μL of 10X restriction buffer [50 mM NaCl, 10 mM tris-Cl(pH=7.5), 10 mM MgCl$_2$, 1 mM dithiothreitol], 63 μL deionized water, and 2 μL EcoRI (20 units/pL) restriction enzyme. To obtain the homologous wheat RuBP fragment (R. Broglie, *Biotechnology*, 1:55 (1983)) 3 uL pW9 (1.3 mg/mL) plasmid is combined with 8 μL of 10X restriction buffer, 67 μL deionized water and 2 μL PST (20 units/pL) restriction enzyme. Both reactions are incubated at 37° C. for 1 hour and subsequently heated to 70° C. for 5 minutes to denature the enzymes. The DNA in 20 μL of each reaction mixture is separated by electrophoresis on a 1.2% agarose gel using 1X TBE (Tris, Borate, EDTA) as buffer. After electrophoresis at 30V, overnight, the gel is washed 2X with 250 mM HCl for 15 minutes, then washed (2X water) and the DNA denatured by soaking the gel in 1.5M NaCl, 0.5M NaOH (2×15 minutes). The denatured gel is washed twice with water and neutralized with 3.0M sodium chloride (NaCl), 0.5M tris HCl pH=7.4 (2×20 mins). The DNA fragments are transferred onto nitrocellulose paper according to Southern (E. M. Southern, *J. Mol. Bio.*, 98:503 (1975)). Panels are prehybridized in 6×SSC, 10×Denhardt's solution (0.2% BSA. 0.2% Ficell, and 0.2% polyvinylpyrolide) containing 100 μg/mL yeast tRNA at room temperature for 1–2 hours. Hybridization is carried out at 52°–54° C. for 16–18 hours.

EXAMPLE 14

A nitrocellulose filter is prepared with both soy and wheat RuBP carboxylase DNA in substantial accordance with the teaching of Example 13 and a single stranded oligonucleotide probe complementary to a target sequence on the 0.8 kb EcoRI fragment of soy RuBP is synthesized. The target portion of the approximate 800 bp DNA fragment has the sequence:

```
              *
3'-CCGTCGAAGGTGTACCAGGT-5'
```

The 20-base probe has the sequence:

```
              *
5'-GGCAGCTTCCACATGGTCCA-3'
```

The sequence for wheat RuBP carboxylase DNA is the same except that an A is substituted for C in the starred position. The effects of the G-A mismatch pairing when soy probe is hybridized with wheat target is determined by comparing the melting temperatures (Tm), the temperature at which 50% of the probe dissociates. The melting temperature of soy probe without 2′-deoxy-3-deazauridine hybridized to soy RuBP DNA and soy probe hybridized to wheat RuBP DNA where there is a single base mismatch present is measured.

The hybridization panel is pretreated with about 15 mLs of 6×SSC buffer (0.9M NaCl, 0.09M sodium citrate), 10X Denhardt's solution and 110 μg/mL yeast tRNA for about 3 hours at 54° C.

Normal oligonucleotide probes containing native bases and probes in which 2′-deoxy-3-deazauridine replaces cytidine in the normal sequence are labelled at the 5′ end with γ-$^{32}$P to a specific activity of about $3.9\times10^6$ cpm/pmole. About 0.15 pmole of labelled soy probe is added to fresh hybridization buffer (10 mL) and the panel is heated in the buffer at about 54° C. for 12 hours. The panel is washed at 58° C. in 6×SSC for 5 minutes and an autoradiogram exposure (24 hours) obtained using a Kodak XAR-5 film with one intensifying screen. Soy RuBP DNA is strongly exposed on the autoradiogram while wheat RuBP DNA is only weakly detectable. The panel is then washed at 60° C. for 5 minutes. The soy DNA signal remains strong and no wheat DNA signal is detected. The panel is then washed at 63° C. and the soy signal is still visible but only to the extent of about half that visible at 60° C. Thus, the melting temperature (Tm) of the soy RuBP probe and soy target DNA is about 63° C. and the Tm for the soy RuBP complement and wheat target DNA is estimated to be about 58° C. The Tm for the probes listed in Example 18, Table III, were determined in a similar manner.

EXAMPLE 15

A soy RuBP probe is constructed in substantial accordance with the teaching of Example 14, including the same sequence, however, the cytidine at position 9 from the 5′ end is replaced with 2′-deoxy3-deazauridine. This probe is 5′ labelled in substantial accordance with the teaching of Example 12 and has the following sequence:

5′-GGCAGCTTYCACATGGTCCA-3′
Y = 2′-deoxy-3-deazauridine

A freshly prepared nitrocellulose panel is employed and the 2′-deoxy-3-deazauridine containing probe is allowed to hybridize, and then washed in substantial accordance with the teaching of Example 14. Washes are conducted at 60°, 70°, 80° and 90° C. The soy specific probes hybridize only to the soy RuBP DNA and are distinctly visible throughout the wash cycle with wheat DNA weakly visible. At 90° C. the intensity of the DNA band in the autoradiogram was about 25% of the intensity observed at 70° C. (Intensity at 70° C. is about equal to 60° C.).

In a separate experiment the soy probe containing 2′-deoxy-3-deazauridine is resynthesized, labelled with $^{32}$P and a freshly prepared nitrocellulose panel is probed. Washes are conducted at temperatures of 64°, 66° and 70° C. Again excellent selectivity and detectability are maintained. A 5 minute wash at 100° C. in 0.1×SSC is accomplished with about one-half of the original (64° C.) concentration of probe remaining hybridized to the soy RuBP DNA.

EXAMPLE 16

The oligonucleotide probe complementary to wheat RuBP DNA is synthesized in substantial accordance with the teaching of Example 12, with 2′-deoxy-3-deazauridine replacing cytidine at position 9 from the 5′ end. The 20-base probe has the following sequence:

5′-GGC AGC TTY CAC ATA GTC CA-3′
Y = 2′-deoxy-3-deazauridine

A freshly prepared nitrocellulose panel is treated with the 2′-deoxy-3-deazauridine containing wheat probe in substantial accordance with the teaching of Example 13. Washes are conducted at 70°, 80° and 90° C. In this instance, the wheat probe detects only the wheat target DNA. At 90° C. about 50% of the original signal remains on the autoradiogram.

EXAMPLE 17

Three 17-base pair probes to the gene for *Bacillus thuringiensis* toxin (B.t.t.) are synthesized in substantial accordance with the teaching of Example 12. One with 2′-deoxy-3-deazauridine replacing cytidine at position 8 from the 5' end (Btt-8), another with 2'-deoxy-3-deazauridine replacing cytidine at position 12 from the 5' end (Btt-12) and the normal probe without 2'-deoxy-3-deazauridine (Btt-N). The probes have the following sequences:

5'-ATG AAT CCG AAC AAT CG-3' (Btt-N)

5'-ATG AAT CYG AAC AAT CG-3'
Y = 2'-deoxy-3-deazauridine (Btt-8)

5'-ATG AAT CCG AAY AAT CG-3'
Y = 2'-deoxy-3-deazauridine (Btt-12)

These probes are $^{32}$P-labeled in substantial accordance with the teaching of Example 12 and used to identify E. coli colonies containing the Btt gene. Seventeen colonies are screened. Three of the E. coli colonies contain the correct Btt gene, the remainder contain only a portion of the Btt gene and do not contain the portion to which the probe is designed to hybridize. Three duplicate colony filters are prepared in which the DNA from the *E. coli* colonies growing in a culture dish is transferred to the filter (ICN Biochemicals, "Protocols for DNA and RNA Transfer, DNA Electrotransfer and Protein Transfer to Biotrans TM Nylon Membranes," 1985, Pall Corporation). One filter is probed with the Btt-N probe; the second filter is probed with Btt-8 and the third probed with Btt-12. The hybridization is carried out at about 40°–42° C. for 20 hours. Each filter is subsequently washed in 1×SSC 1% SDS (sodium dodecyl sulfate) for 3 minutes at 45° C. This wash is repeated and the filters are exposed to x-ray film for 4 hours. All three probes hybridize to the same colonies, all of which contain the correct Btt gene.

The filters are then washed at 65° C. for 5 minutes in 1×SSC 1% SDS. The normal probe, Btt-N, is completely removed at this temperature, however, both Btt-8 and Btt-12 containing 2′-deoxy-3-deazauridine remain hybridized to the colonies containing the Btt gene. The two 2′-deoxy-3-deazauridine containing probe filters are washed for 1 hour in 50% formamide containing about 10 mM sodium phosphate ($Na_2PO_4$), pH 6.5 at 65° C. Both Btt-8 and Btt-12 are still hybridized after treatment and easily detected by autoradiography.

EXAMPLE 18

Single-stranded oligonucleotide probes are synthesized in accordance with Example 12, without 2′-deoxy-3-deazauridine and with 2′-deoxy-3-deazauridine (indicated by "Y") substituted for a cytidine. The probes are hybridized with complementary target DNA, and the corresponding melting temperatures are compared as shown in Table III. The hybrid molecules generated with probes containing 2′-deoxy-3-deazauridine have considerably higher apparent melting temperatures than hybrid molecules containing probes without 2′-deoxy-3-deazauridine. Table III lists probes of the invention complementary to soybean ribulose bis-, phosphate (RuBP) carboxylase small subunit DNA (soy), wheat RuBP carboxylase small subunit DNA (wheat), the gene for *Bacillus thuringiensis* toxin (Btt) and human cytomegalovirus gene (HCV). Control probes (not shown) have the same sequences as the probes shown in Table III, however, control probes have a cytidine in place of "Y".

TABLE III

| Probe Sequence | | | | | |
|---|---|---|---|---|---|
| Target | Probe Sequence (5′-3′) | Probe Length | HT** | Tm* Control Probes | Tm* Probes of the Invention |
| soy | AGCT TCC AYA TGG TCC | 16 mer | 40 | 56 | >90° C. |
| soy | AGCT TCC AYA TGG TCC A | 17 mer | 45 | ~58 | >90° C. |
| soy | GCA GCT TYC ACA TGG TCC | 18 mer | 45 | 60 | >90° C. |
| soy | GGCA GCT TYC ACA TGG TCC A | 20 mer | 52 | 63 | >90° C. |
| wheat | GGC AGC TTY CAC ATA GTC CA | 20 mer | 52 | ~65 | >90° C. |
| Btt | ATG AAT CYG AAC AAT CG | 17 mer | 41 | <65 | >90° C. |
| Btt | ATG AAT CCG AAY AAT CG | 17 mer | 41 | <65 | >90° C. |
| HCV | TAG CGG CGA CGY ACG TAC AC | 20 mer | 52 | ND | >90° C. |
| HCV | CTC TAG GYT GTC GGC CAG CC | 20 mer | 52 | ND | >90° C. |
| soy | TAG GCA GCT TCC AYA TGG TCC AGT AGC | 27 mer | 40 | 76 | >90° C. |

Y = 2′-deoxy-3-deazauridine
*Temperature at which approximately ½ the signal of labeled probe remains
**Hybridization temperature °C.

EXAMPLE 19

A soy RuBP probe is constructed in substantial accordance with the teaching of Example 14, including the same probe sequence, however, the cytidine at position 19 (from the 5′-end) is replaced with 2′-deoxy-3-deazauridine:

5′-GGC AGC TTC CAC ATG GTC YA-3′
Y = 2′-deoxy-3-deazauridine

This probe is $^{32}$-P labelled in substantial accordance with the teaching of Example 12 and employed in a Southern experiment using a freshly prepared nitrocellulose blot in substantial accordance with Example 14. The extent of hybridization of the probe is about equal to both soy and wheat DNA at 60° C. Other washes are conducted at 63° C., 70° C. and 83° C. After the 83° C. wash, about 15% of the concentration distinguishable at 63° C. still remains distinguishable for both soy and wheat RuBP DNA sequences.

EXAMPLE 20

A soy RuBP probe is constructed in substantial accordance with the teaching of Example 14, including the same sequence, however, the cytidine at position 9 (from the 5′end) is replaced with 4-O-diphenylcarbamoyl-3-iodo-1- (2-deoxy-beta-D-erythio-pentofuranosyl)-2(1H)-pyridone (30), which becomes 3-iodo-4-hydroxy-1-(2-deoxy-beta-D-erythio-pentofuranosyl)-2(1H)pyridone, after deprotection. This probe is $^{32}$-P labelled in substantial accordance with the teaching of Example 12 and has the following sequence:

```
5'-GGC AGC TTX CAC ATG GTC CA-3'
X = 3-iodo-4-hydroxy-1-(2-deoxy-beta-D-
    erythro-pentofuranosyl)-2(1H)-
    pyridone.
```

A freshly prepared nitrocellulose panel is employed and the 3-iodo-4-hydroxy-1-(2-deoxy-beta-D-erythiopentofuranosyl)-2(1H)-pyridone (12) containing probe allowed to hybridize in substantial accordance with the teaching of Example 12, however, in this case 6 picomole of $^{32}$-P radiolabelled probe is employed. Washes are accomplished in substantial accordance with the teaching of Example 21. At 80° C. about 50% of the concentration visible at 60° C. still remains visible. Therefore, the apparent Tm (at which 50% of the signal remains) is about 80"C.

EXAMPLE 21

A soy RuBP probe is constructed in substantial accordance with Example 20, however, X=5-iodo-4-hydroxy-1-(2-deoxy-beta-D-erythro-pentofuranosyl)-2 (1H)-pyridone, which is 4-O-diphenylcarbamoyl-5-iodo-1-(2-deoxy-beta-D-erythio-pentofuranosyl)-2(1H)-pyridone (31) prior to deprotection. A freshly prepared nitrocellulose panel is employed and hybridization carried out at 52° C. with 3 picomoles of $^{32}$-P labelled probe. Washes are conducted at 58°, 63°, 70°, 80° and 100° C. in 6×SSC for 5 minutes. At 100° C. approximately 50% of the signal visible at 63° C. (the Tm of the probe without 5-iodo-4-hydroxy-1-(2-deoxy-beta-D-erythiopentofuranosyl)-2 (1H)-pyridone (13 ) ) still remains visible. Therefore, the apparent Tm (at which 50% of the signal remains) is about 100° C. Both soy and wheat RuBP DNA are visible to an equal extent. When the hybridization is carried out at 37° C., and the panel washed at 80° C. about 25% of the concentration visible at 60° C. still remains visible.

EXAMPLE 22

A soy RuBP probe is constructed in substantial accordance with the teaching of Example 20, however, X=4-O-diphenylcarbamoyl-3-ethenyl-1-(2-deoxy-beta-D-erythio-pentofuranosyl)-2(1H)-pyridone (37). A freshly prepared nitrocellulose panel is employed and hybridization carried out at 53° C. with $^{32}$-P labelled probe. In this case, the autoradiographic signal for both soy and wheat sequences were equally intense after washing at 63° C. for 5 minutes. Further washes were conducted at 69°, 80° and 100° C. About 75% of the signal visible at 63° C. (the Tm of the probe without 4-O-diphenylcarbamoyl-3-ethenyl-1 (2-deoxy-beta-D-erythio-pentofuranosyl)-2(1H)-pyridone (37)) remains at 80° C. for both soy and wheat DNA. About 10% of the signal visible at 63° C. remains after the 100° C. wash. Therefore, the apparent Tm (at which 50% of the signal remains) is about 80° C.

EXAMPLE 23

A soy RuBP probe is constructed in substantial accordance with the teaching of Example 14, however, the probe (Soy 27 ) is extended to include 27 bases of soy sequence:

```
5' TAG GCA GCT TCC ACA TGG TCC AGT AGC 3'
(Soy 27)
``` and the cytidine at position 14 from the 5' end is replaced with 2'-deoxy-3-deazauridine:

```
5' TAG GCA GCT TCC AYA TGG TCC AGT AGC 3'
Y = 2'-deoxy-3-deazauridine.
```

The probe is $^{32}$P-labelled and hybridized to a freshly prepared panel in substantial accordance with Example 14, except the hybridization temperature is 40° C. Washes are carried out at 66°, 75°, 79°, 90° and 100° C. Both soy and wheat DNA are visualized to an equal extent throughout the wash cycle. At 90° C. about 25% of the DNA visible at 79° C. still remains visible. At 100° C. the signal is weak but still easily discernible.

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein.

What is claimed is:

1. A compound of the formula:

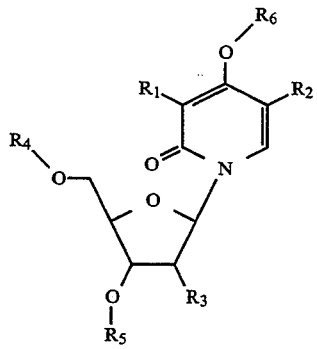

in which
R$_1$ and R$_2$ independently are C$_1$-C$_5$ alkyl, C$_2$-C$_5$ alkenyl, halo or hydrogen,
R$_3$ is hydrogen, halo, C$_1$-C$_5$ alkoxy or tri(C$_1$-C$_5$ alkyl) substituted silyloxy,
R$_4$ is triphenylmethyl or mono-, di- or tri (C$_1$-C$_5$ alkoxy) substituted triphenylemethyl,
R$_5$ is hydrogen phosphonate

in which R' is B- cyanoethyl, C$_1$-C$_5$ alkoxy, or C$_1$-C$_5$ alkyl, and R" is morpholino, or mono- or di(C$_1$-C$_5$ alkyl) substituted amino, and
R$_6$ is tri(C$_1$-C$_5$ alkyl or C$_1$-C$_5$ alkoxy) substituted silyloxy, benxoyl, methylcarbonyl, carbamoyl, or carbamoly substituted with C$_1$-C$_5$ alkyl, phenyl, acetyl or isobutyryl.

2. The compound of claim 1 in which R$_1$, R$_2$ and R$_3$ are hydrogen, R$_4$ is dimethoxytriphenylmethyl, R' is β-cyanoethyl, R" is N,N-diisopropyl amino and R$_6$ is diphenylcarbamoyl.

3. The compound of claim 1 in which $R_1$ and $R_2$ are hydrogen, $R_3$ is triisopropylsilyloxy, $R_4$ is dimethoxytriphenylmethyl, R' is β-cyanoethyl, R" is N,N-diisopropyl amino and $R_6$ is diphenylcarbamoyl.

4. The compound of claim 1 in which $R_1$ and $R_2$ are hydrogen, $R_3$ is tert-butyl-dimethylsilyloxy, $R_4$ is dimethoxytriphenylmethyl, R' is β-cyanoethyl, R" is N,N-diisopropyl amino, and $R_6$ is diphenylcarbamoyl.

5. The compound of claim 1 in which $R_1$ is iodine, $R_2$ is hydrogen, $R_3$ is hydrogen, $R_4$ is dimethoxytriphenylmethyl, R' is β-cyanoethyl, R" is N,N-diisopropyl amino and $R_6$ is diphenylcarbamoyl.

6. The compound of claim 1 in which $R_1$ is iodine, $R_2$ is hydrogen, $R_3$ is triisopropylsilyloxy, $R_4$ is dimethoxytriphenylmethyl, R' is β-cyanoethyl, R" is N,N-diisopropyl amino and $R_6$ is diphenylcarbamoyl.

7. The compound of claim 1 in which $R_1$ is hydrogen, $R_2$ is iodine, $R_3$ is triisopropylsilyloxy, $R_4$ is dimethoxytrityl, R' is p-cyanoethyl, R" is N,N-diisopropyl amino and $R_6$ is diphenylcarbamoyl.

8. The compound of claim 1 in which $R_1$ is hydrogen, $R_2$ is iodine, $R_3$ is hydrogen, $R_4$ is dimethoxytriphenylmethyl, R' is β-cyanoethyl, R" is N,N-diisopropyl amino and $R_6$ is diphenylcarbamoyl.

9. The compound of claim 1 in which $R_1$ is ethenyl, $R_2$ is hydrogen, $R_3$ is triisopropylsilyloxy, $R_4$ is dimethoxytriphenylmethyl, R' is β-cyanoethyl, R" is N,N-diisopropyl amino and $R_6$ is diphenylcarbamoyl.

10. The compound of claim 1 in which $R_1$ is ethenyl, $R_2$ is hydrogen, $R_3$ is hydrogen, $R_4$ is dimethoxytriphenylmethyl, R' is β-cyanoethyl, R" is N,N-diisopropyl amino and $R_6$ is diphenylcarbamoyl.

* * * * *